United States Patent
Bergman et al.

(10) Patent No.: US 12,070,278 B2
(45) Date of Patent: Aug. 27, 2024

(54) BRAIN NAVIGATION LEAD POSITIONING AND METHODS THEREOF

(71) Applicant: Alpha Omega Engineering Ltd., Nof HaGalil (IL)

(72) Inventors: Hagai Bergman, Jerusalem (IL); Salam Aukal, Shefa-Amr (IL)

(73) Assignee: Alpha Omega Engineering Ltd., Nof HaGalil (IL)

( * ) Notice: Subject to any disclaimer, the term of this patent is extended or adjusted under 35 U.S.C. 154(b) by 421 days.

(21) Appl. No.: 17/622,337

(22) PCT Filed: Jun. 26, 2020

(86) PCT No.: PCT/IL2020/050718
§ 371 (c)(1),
(2) Date: Dec. 23, 2021

(87) PCT Pub. No.: WO2020/261282
PCT Pub. Date: Dec. 30, 2020

(65) Prior Publication Data
US 2022/0241023 A1    Aug. 4, 2022

(51) Int. Cl.
*A61N 1/05*    (2006.01)
*A61B 34/20*    (2016.01)
*A61N 1/36*    (2006.01)

(52) U.S. Cl.
CPC .......... *A61B 34/20* (2016.02); *A61N 1/0534* (2013.01); *A61N 1/36128* (2013.01); *A61B 2034/2046* (2016.02)

(58) Field of Classification Search
CPC ...... A61B 2034/107; A61B 2034/2046; A61B 2505/05; A61B 34/20; A61B 34/25;
(Continued)

(56) References Cited

U.S. PATENT DOCUMENTS 8,280,514 B2 * 10/2012 Lozano ............... A61B 5/4082
607/45
8,792,972 B2    7/2014 Zaidel et al.
(Continued)

FOREIGN PATENT DOCUMENTS

WO    WO 2018/008034    1/2018
WO    WO 2020/261282    12/2020

OTHER PUBLICATIONS

International Search Report and the Written Opinion Dated Oct. 7, 2020 From the International Searching Authority Re. Application No. PCT/IL2020/050718. (36 Pages).
(Continued)

*Primary Examiner* — George Manuel

(57) ABSTRACT

A method for determining position of an electrode lead inside a body tissue, including:
  receiving electrical signals recorded from at least one macro electrode contact of an electrode lead positioned inside a body tissue;
  extracting spiking (SPK) signals from the received electrical signals;
  providing stored measurements or indications thereof;
  determining a position of the lead and/or the at least one macro electrode contact inside said body tissue based on the extracted SPK signals and the provided stored measurements or indications thereof.

20 Claims, 13 Drawing Sheets

(58) Field of Classification Search
CPC ..... A61B 5/065; A61B 5/4064; A61B 5/4848; A61B 5/685; A61B 5/6852; A61B 5/6868; A61B 5/6885; A61B 5/6886; A61B 5/7225; A61B 5/7246; A61N 1/0534; A61N 1/36067; A61N 1/36128; A61N 1/36135; A61N 1/37217
See application file for complete search history.

(56) References Cited

U.S. PATENT DOCUMENTS

| | | |
|---|---|---|
| 2005/0065427 A1 | 3/2005 | Magill et al. |
| 2007/0185544 A1 | 8/2007 | Dawant et al. |
| 2012/0101552 A1 | 4/2012 | Lazarewicz et al. |
| 2017/0113046 A1 | 4/2017 | Fried et al. |
| 2019/0069797 A1 | 3/2019 | Naor et al. |

OTHER PUBLICATIONS

International Preliminary Report on Patentability Dated Jan. 6, 2022 From the International Bureau of WIPO Re. Application No. PCT/IL2020/050718. (32 Pages).

Supplementary European Search Report and the European Search Opinion Dated Jun. 16, 2023 From the European Patent Office Re. Application No. 20831347.8. (9 Pages).

* cited by examiner

MER phase

Lead recording

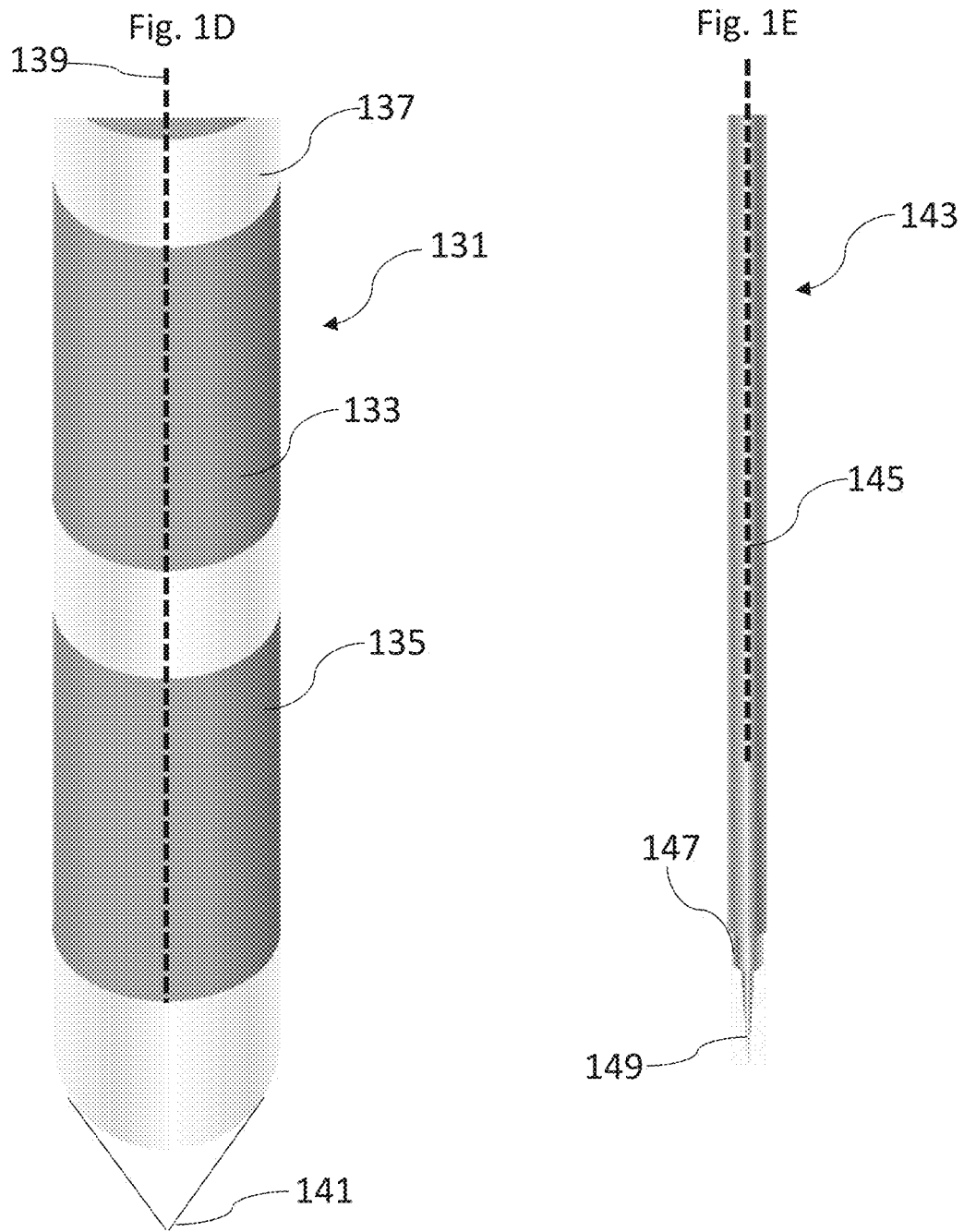

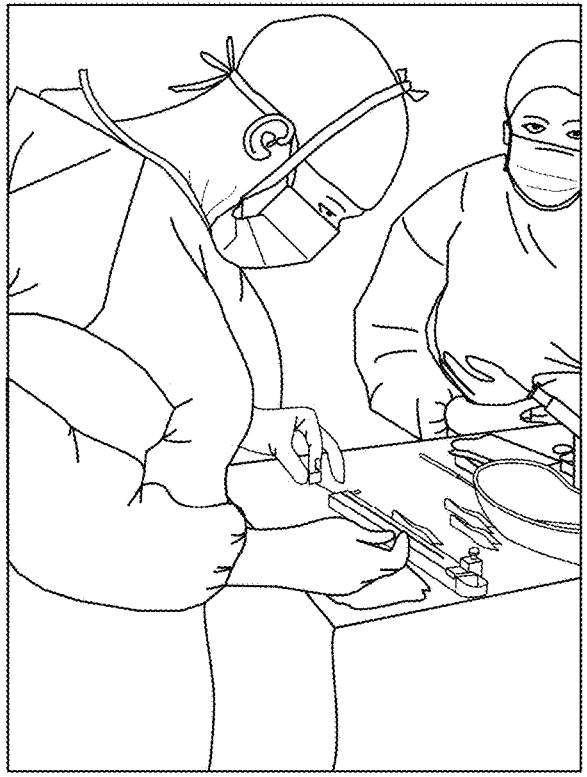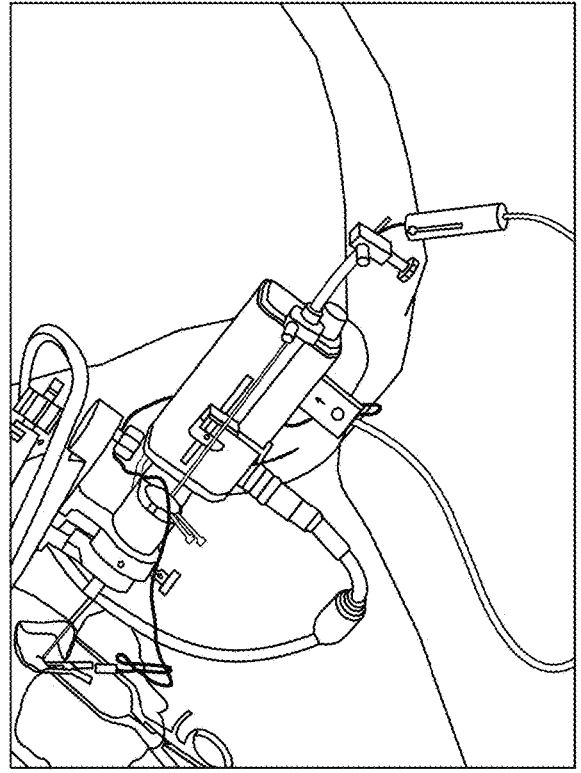
FIG. 1F
(prior art)
FIG. 1G

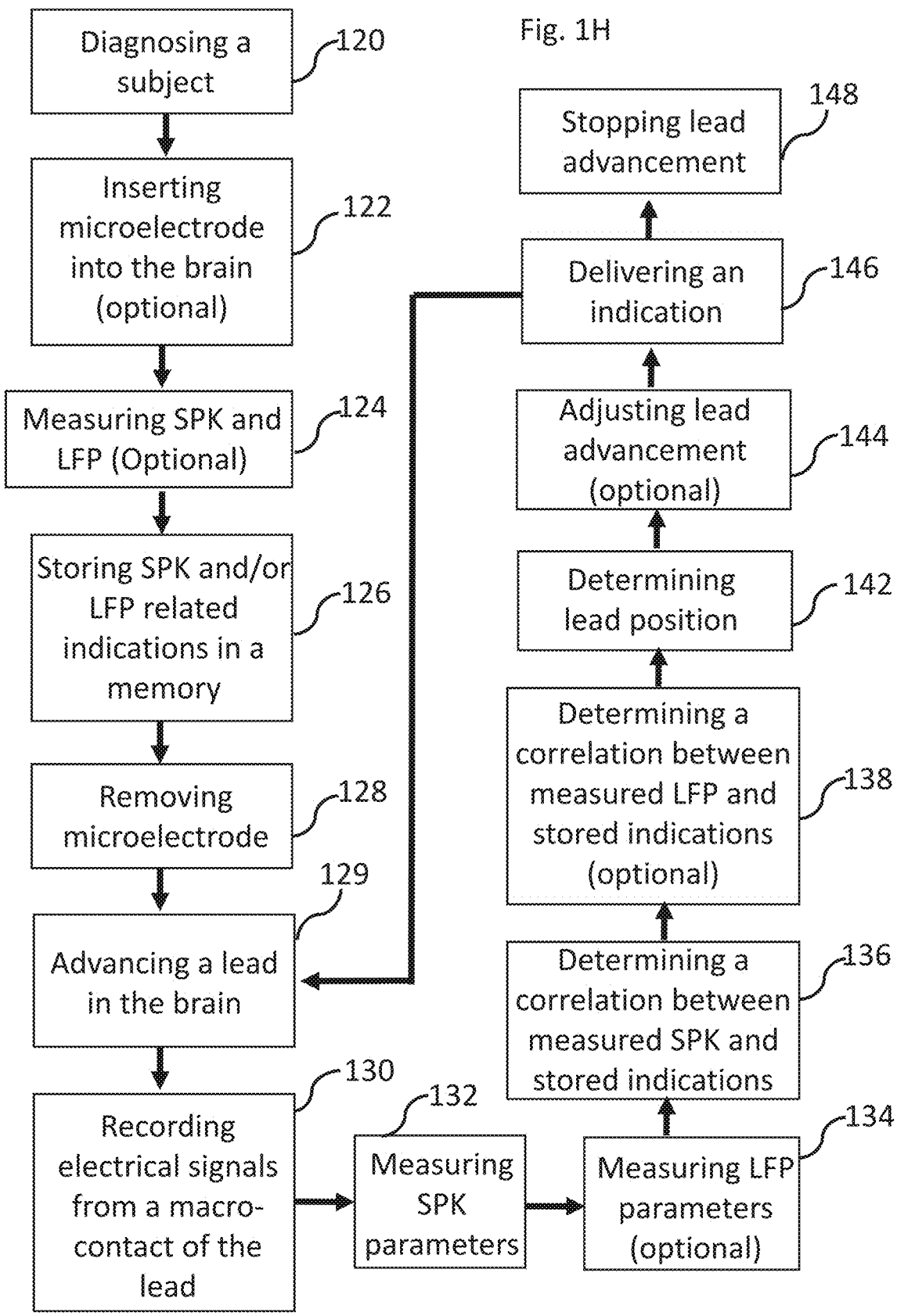

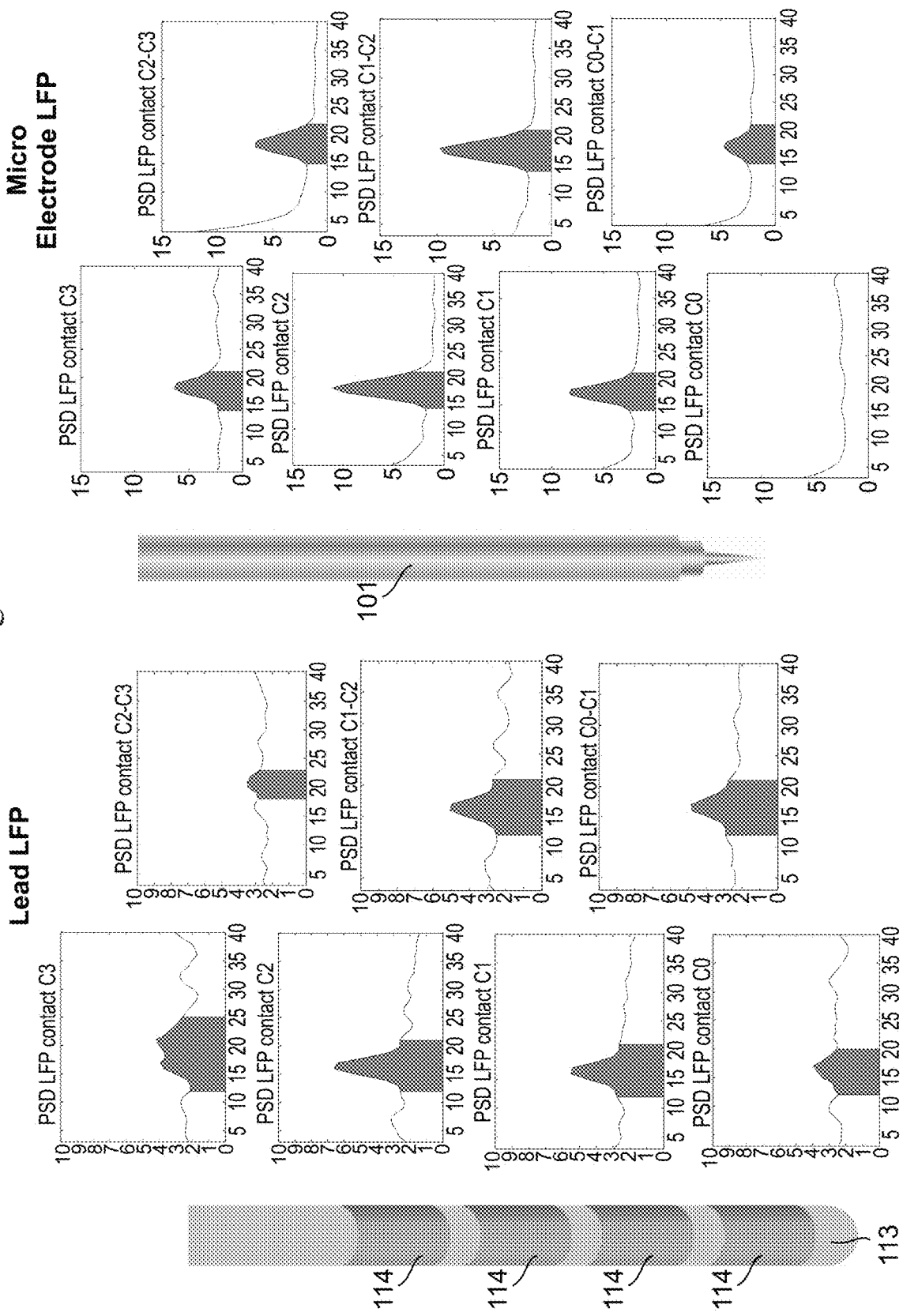

BRAIN NAVIGATION LEAD POSITIONING AND METHODS THEREOF

RELATED APPLICATIONS

This application is a National Phase of PCT Patent Application No. PCT/IL2020/050718 having International filing date of Jun. 26, 2020, which claims the benefit of priority under 35 USC § 119(e) of U.S. Provisional Patent Application No. 62/867,222 filed on Jun. 26, 2019.

PCT Patent Application No. PCT/IL2020/050718 is also related to PCT Patent Application No. PCT/IL2017/050328 filed on 14 Mar. 2017, U.S. patent application Ser. No. 12/658,351, now U.S. Pat. No. 8,792,972 filed on 5 Feb. 2010, and U.S. patent application Ser. No. 16/084,664 filed on 14 Mar. 2017.

The contents of the above applications are all incorporated by reference as if fully set forth herein in their entirety.

FIELD AND BACKGROUND OF THE INVENTION

The present invention, in some embodiments thereof, relates to a navigation lead and system and/or parts thereof and, more particularly, but not exclusively, to methods of positioning a brain navigation lead comprising electrode contacts and configured to measure electrical activity of brain tissue.

Electric field application to the brain is under increasing use for such varied purposes as treatment of neurological and psychiatric conditions. A typical electrical brain stimulation system comprises a pulse generator operatively connected to the brain by a lead. Prior to electric field application from the stimulation lead, a microelectrode probe is often used to determine the desired target location for electric field application, in a process termed microelectrode recording (MER). Then, the microelectrode probe is removed and the stimulation lead for applying the electric field is inserted.

The stimulation target may be a subcortical nucleus or region, and then it would be termed deep brain stimulation (DBS), or it may be in a cortical region, or a region in the spinal cord.

Microelectrode recording (MER) is used in many Deep Brain Stimulation (DBS) cases to identify the target nucleus location based on electrophysiological signals, to delineate borders of the target nucleus and internal borders between nucleus sub-domains, and finally, to determine an optimal location for implantation of the DBS lead. MER relies on recording brain activities, typically "spike" activities from multiple units and/or single units in the 300-6000 Hz frequency range, to determine the target position in the brain and navigate to recommend the DBS Lead position for implantation.

Surgeries for positioning a stimulation lead are typically based on anatomic targeting techniques, involving imaging of the patient brain with a CT and/or MRI machine, defining the anatomical target coordinates and planning a trajectory to reach the anatomical coordinates from the skull with minimal risk to the tissue. The trajectory is executed in the operating room using a stereotactic frame, or a similar "frameless" stereotactic solution, that is firmly fixed to the patient's skull bones and allows to insert and advance tools in the brain according to the planned trajectory. However, physiological verification of these targets is an important step before final implantation of the DBS electrode, allowing, for example, correction of anatomic inaccuracies occurring due to image distortion, brain shift, cerebrospinal fluid loss, and pneumocephalus, all of which can lead to final target deviation. Regardless of potential deviations from the planned target, the verification process also allows, for example, to account for the tissue physiology in selecting the implantation location. The process of physiological verification is also termed "navigation".

Thus, neurophysiological techniques are necessary to refine lead positioning within a target and to optimize clinical outcomes and minimize stimulation-related side effects. The neurophysiological techniques include the MER described above, and may also include a step of testing the effect of stimulation at the presumed optimal depth, to verify that the stimulation indeed has an effect of symptom reduction and does not cause disturbing side effects. This step is relevant in some DBS surgeries but usually less relevant when the symptoms of the treated disorder do not respond at a time frame of seconds or several minutes.

After mapping the brain with the microelectrode, and determining the optimal depth for lead implantation, the neurosurgeon extracts the microelectrode out of the brain and then inserts the DBS Lead to position it at the optimal depth determined at the microelectrode navigation phase. FIG. 1F depicts a neurosurgeon measuring the DBS on a specifically designed ruler apparatus, in order to fix a mechanical stopper at the correct position along the lead axis, such that when inserted into the brain it would be stopped (by a feature of the external mechanical apparatus) at the correct depth.

The various microelectrodes and DBS Leads are described more fully in PCT/IL2017/050328, incorporated herein by reference in its entirety.

Micro contacts are known to be specifically suitable for spike activity recordings (sampling rate of at least 10 KHz, approximately 300-6000 Hz filters);

Macro contacts are known to be suitable for local field potential (LFP) recordings (sample rate can be approximately 500 Hz, or 1375 Hz, or higher, approximately 0.07-300 Hz filters).

SUMMARY OF THE INVENTION

The invention is driven, for example by two limitations of the commonly practiced lead positioning process described above. The first limitation is the method of preparing the lead for insertion into the optimal position in the brain. This method relies on a manual length measurement with a ruler along the lead axis, and manual positioning of a mechanical stopper at the correct location on the axis. DBS outcomes may be affected by deviations on the order of 0.5 mm, and the errors introduced by this process alone may reduce the efficacy of the DBS procedure. The second limitation is in the necessity to perform a 2-stage process, the $1^{st}$ stage being the neurological navigation with a Microelectrode and the $2^{nd}$ stage the positioning of the lead at an optimal position. The 2-stage process imposes time consumption in handling and preparing both the Microelectrode and the DBS lead, expenses related to using an additional mapping device and related accessories in addition to the implantable DBS lead, and positioning errors in the process of removing the Microelectrode and positioning the DBS lead at the optimal position.

Following are some examples of some embodiments of the invention. Features of one example may be combined with one or more features and/or other examples:

In accordance with an embodiment of the invention, a system for brain navigation lead positioning, the system comprising an insertable implantable lead comprising a plurality of contacts comprising at least one macro contact and at least one micro contact; the implantable lead insertable to reach a predetermined target; the implantable lead plurality of contacts each operatively connectable to a computer medium, the computer medium capable of performing at least one of the following functions: obtaining readings from at least one of the plurality of contacts during advancement of the implantable lead, comparing the readings, calculating at least one similarity measure between the readings, determining location of the implantable lead based on the similarity measure, providing recommendations based on the location determining.

In some embodiments, the readings are comprised of LFP and SPK components. Further In some embodiments, the readings are obtained using one of monopolar, bi-polar and differential recordings. Still further in some embodiments, the step of obtaining readings comprises filtering of the readings into one of LFP and SPK components, wherein the LFP filter is within the range of 0.07-300 HZ and the SPK filter is within the range of 300-6000 Hz. Yet further in some embodiments, the step of obtaining readings further comprises full-wave rectification and calculation of PSD estimates from the readings.

In accordance with an embodiment of the invention, the comparing of the readings comprises comparison between LFP and SPK components obtained from the Implantable Lead. In some embodiments, determining of location is based on the similarity measures, wherein the location with the highest similarity measure value with the location determined as optimal from the lead recording and optionally stimulating, is indicated as the best location. Further in some embodiments, the similarity measure comprises similarity between processed Micro contact SPK readings and processed Macro contact SPK readings. Still further in some embodiments, at least one of the Micro contact and the Macro contact of the Implantable Lead are configured to deliver stimulation. Yet further in some embodiments, the recommendations comprise at least one of: Go/No Go output and Degree of advancement output and direction of advancement. Advantageously, the readings are obtained from at least one of multiple patients and multiple trajectories.

In accordance with an embodiment of the invention, the computer medium is capable of at least one of learning a relation between at least one of the SPK and LFP components and location along the trajectory or learning a relation between the SPK and LFP components and optimal implantation target.

In some embodiments, the computer medium is capable of providing at least semi-automatic or automatic navigation to a target. Further in some embodiments, the system comprising an insertable microelectrode. Still further in some embodiments, the insertable microelectrode comprising at least one of microelectrode contact and macroelectrode contact.

In accordance with an embodiment of the present invention, a method for determining a position of a brain implantable lead, comprising: providing electrical signals which at least partly comprise SPK signals measured by one or more macro electrode contacts of a brain implantable lead; calculating a similarity measure between the provided electrical signals and stored indications related to one or both of previously measured SPK signals and LFP signals; determining a position of the brain implantable lead or portions thereof based on the calculation results.

In some embodiments, the provided electrical signals comprise LFP signals. Further in some embodiments, the calculating comprises identifying a highest similarity value between the provided electrical signals and the stored indication, and wherein the determining comprises determining the position based on the highest similarity value. Further in some embodiments, the calculating comprises identifying a highest similarity measure value between the provided electrical signals and the stored indication, and wherein the determining comprises determining the position based on the highest similarity measure value. Still further in some embodiments, the SPK signals comprise electrical signals in a frequency range of 300-6000 Hz. Yet further in some embodiments, the similarity measure value is larger than a predetermined value. Advantageously, the predetermined value is 0.8.

Some examples of some embodiments of the invention are listed below. Features from one example may be combined with features from other examples:

Example 1. A method for determining position of an electrode lead inside a body tissue, comprising:
  receiving electrical signals recorded from at least one macro electrode contact of an electrode lead positioned inside a body tissue;
  extracting spiking (SPK) signals from said received electrical signals;
  providing stored measurements or indications thereof;
  determining a position of said lead and/or said at least one macro electrode contact inside said body tissue based on said extracted SPK signals and said provided stored measurements or indications thereof.

Example 2. A method according to example 1, wherein said provided stored measurements or indications thereof are measured by at least one microelectrode inside said body tissue.

Example 3. A method according to any one of examples 1 or 2, wherein said determined position is a position relative to at least one of, a position inside said body tissue, a position along an insertion trajectory of said electrode lead inside the body tissue, a position of an entry point of said lead into a skull, and a position of an entry point of said lead into a brain.

Example 4. A method according to any one of the previous examples, wherein said stored measurements or indications thereof comprise SPK measurements or indications thereof.

Example 5. A method according to any one of the previous examples, wherein said stored measurements or indications thereof comprise LFP measurements or indications thereof.

Example 6. A method according to any one of the previous examples, comprising:
determining a correlation between said extracted spiking signals and said stored measurements or indications thereof, and wherein said determining said position comprises determining said position based on said determined correlation.

Example 7. A method according to any one of the previous examples, wherein said extracting comprises extracting local field potential (LFP) signals from said received electrical signals.

Example 8. A method according to example 7, wherein said extracting comprises filtering said received electrical signals to get LFP signals in a frequency range of 0.1 Hz-300 Hz.

Example 9. A method according to any one of examples 7 or 8, wherein said determining comprises determining a relative position of said lead and/or said at least one macro electrode contact inside said body based on said extracted spiking signals and/or said extracted LFP signals.

Example 10. A method according to example 9, comprising:
determining a correlation between said extracted spiking signals and/or said extracted LFP signals and said stored measurements or indications thereof, and wherein said determining said relative position comprises determining said relative position based on said determined correlation.

Example 11. A method according to example 10, wherein said determining a relative position comprises determining a relative position based on a determined correlation with the highest correlation value.

Example 12. A method according to any one of the previous examples comprising recording said electrical signals in a sampling rate in a range of 15 KHz-50 KHz.

Example 13. A method according to any one of the previous examples, wherein said received electrical signals are in a frequency range of 0.5 Hz-6000 Hz.

Example 14. A method according to any one of the previous examples, wherein said extracting comprises filtering said received electrical signals to obtain said SPK signals in a range of 300 Hz-6000 Hz.

Example 15. A method according to example 14, wherein said extracting comprises reconstructing a waveform from said obtained said SPK signals.

Example 16. A method according to example 15, wherein said reconstructing comprises applying a full wave rectification algorithm on said SPK signals.

Example 17. A method according to any one of examples 14 to 16, comprising:
measuring at least one parameter of said extracted spiking signals, and wherein said determining a position comprises determining a relative position of said electrode lead and/or said at least one macro electrode contact inside said body tissue based on said measured at least one parameter and said provided stored measurements or indications thereof.

Example 18. A method according to example 17, wherein said at least one parameter of said extracted spiking signals comprises power spectrum density (PSD) or normalized PSD.

Example 19. A method according to any one of examples 17 or 18, wherein said at least one parameter of said extracted SPK comprises at least one of Amplitude, Power, Frequency, Spike detection, Audio, Area under a curve, root mean square (RMS) and firing rate.

Example 20. A method according to any one of the previous examples, wherein said receiving comprises receiving said electrical signals from an electrode lead advancing through said body tissue towards a desired anatomical target.

Example 21. A method according to example 16, comprising:
delivering a human detectable indication according to a relation between said determined relative position and a desired anatomical target.

Example 22. A method according to example 21, wherein said delivering comprises delivering instructions regarding at least one of advancement speed of said electrode lead, advancement step size of said electrode lead, advancement direction of said electrode lead, according to said relation.

Example 23. A method according to any one of examples 21 or 22, wherein said delivering comprises delivering instructions to stop the advancement of said electrode lead if said relation indicates that said relative position is at a distance smaller than 0.5 mm from said desired anatomical target.

Example 24. A method according to any one of the previous examples, wherein said body tissue comprises the brain, and wherein said lead comprises a DBS lead configured to deliver an electric stimulation to brain tissue.

Example 25. A method for determining a position of a deep brain stimulation (DBS) lead inside the brain, comprising:
receiving electrical signals recorded from at least one macro electrode contact of a deep brain stimulation (DBS) lead positioned inside a brain;
processing said electrical signals;
providing stored measurements or indications thereof;
performing two or more correlations between said processed electrical signals and said stored measurements or indications thereof;
calculating a correlation value for each of said two or more correlations;
determining a position of said DBS lead and/or said at least one macro electrode contact inside said body tissue based on a correlation with the highest correlation value.

Example 26. A method according to example 25, wherein said stored measurements or indications thereof comprise at least one of SPK measurements and/or LFP measurements.

Example 27. A method according to any one of examples 25 or 26, wherein said stored measurements or indications thereof are measurements of electrical signals recorded by at least one microelectrode.

Example 28. A method according to example 27, wherein said stored measurements or indications thereof are measurements of electrical signals recorded by at least one micro contact and/or at least one macro contact of said microelectrode.

Example 29. A method according to any one of examples 25 to 28, wherein said determining comprises determining a position of said lead if said highest correlation value is larger than 0.8.

Example 30. A method according to any one of examples 25 to 29, comprising:
delivering a human detectable indication with recommendations to modify at least one parameter of an advancement of said DBS lead according to said determined position.

Example 31. A method according to example 30, wherein said at least one advancement parameter of said DBS lead comprises at least one of, advancement speed, advancement direction, and advancement step size.

Example 32. A method according to any one of examples 25 to 31, wherein said determined position is a position relative to at least one of a position inside said brain, a position along an insertion trajectory of said macro electrode contact inside the body tissue, a position of an entry point of said lead into a skull, and a position of an entry point of said lead into a brain.

Example 33. A system for determining a position of a lead inside a subject body, comprising:
an implantable lead insertable via an insertion trajectory through body tissue, comprising at least one macro electrode contact configured to record electrical signals from tissue surrounding said implantable lead;
a control unit connectable to said implantable lead, comprising:
a memory, wherein said memory stores one or more indications including a relation between a position in said body tissue and electrical measurements or indications thereof;
a control circuitry connected to said at least one macro electrode, wherein said control circuitry is configures to:
receive electrical signals recorded by said at least one macro-electrode contact;

extract SPK signals from said received electrical signals;

measure values of at least one SPK parameter from said extracted SPK signals;

determine a position of said implantable lead and/or said macro electrode contact in said body using said measured at least one SPK parameter and said stored indications.

Example 34. A system according to example 33, wherein said control circuitry is configured to calculate a relation value between said measured SPK signals and one or more indications stored in said memory, and to determine a position of said implantable lead in said body based on said calculated relation value.

Example 35. A system according to any one of examples 33 or 34, wherein said control circuitry is configured to filter said received electrical signal with a filter which extracts electrical signals in a frequency range of 250 Hz-7000 Hz, and to measure values of said at least one SPK parameter from said filtered signals.

Example 36. A system according to example 35, wherein said control circuitry is configured to reconstruct a waveform from said filtered signals, and to measure said at least one SPK parameter from said reconstructed waveform.

Example 37. A system according to example 36, wherein said control circuitry is configured to apply a full wave rectification algorithm on said filtered signals to said reconstruct said waveform.

Example 38. A system according to any one of examples 33 to 37, wherein said at least one SPK parameter comprises power spectrum density (PSD).

Example 39. A system according to any one of examples 33 to 38, wherein said at least one SPK parameter comprises at least one of amplitude, power, frequency, spike detection, Audio, Area under a curve, root mean square (RMS) and firing rate.

Example 40. A system according to any one of examples 33 to 39, wherein said control circuitry is configured to:

extract LFP signals from said received electrical signals;

measure values of at least one LFP parameter from said extracted LFP signals;

determine a position of said implantable lead and/or said macro electrode contact in said body using said measured at least one LFP parameter and said stored indications.

Example 41. A system according to example 40, wherein said control circuitry is configured to filter said received electrical signal with a filter which extracts electrical signals in a frequency range of 0.5 Hz-350 Hz, and to measure values of said at least one LFP parameter from said filtered signals.

Example 42. A system according to any one of examples 40 or 41, wherein said at least one LFP parameter comprises power spectrum density (PSD).

Example 43. A system according to any one of examples 40 to 42, wherein said at least one LFP parameter comprises at least one of amplitude, power, frequency, spike detection, Audio, Area under the curve, root mean square (RMS) and firing rate.

Example 44. A system according to any one of examples 40 to 43, wherein said control circuitry is configured to:

calculate a first correlation value between said at least one measured SPK parameter and said stored indications, and a second correlation value between said at least one measured LFP parameter and said stored indications;

select a correlation with the highest correlation value from said first correlation value and said second correlation value; and determine a position of said lead and/or said at least one macro electrode contact based on said selected correlation.

Example 45. A system according to any one of examples 33 to 44, comprising:

a user interface configured to deliver at least one human detectable indication to a user of the system; and wherein said control circuitry signals said user interface to generate said human detectable indication according to said determined position.

Example 46. A system according to example 45, wherein said at least one human detectable indication comprises recommendations regarding an advancement speed of the lead, an advancement direction of said lead, an advancement step size.

Example 47. A system according to any one of examples 33 to 45, comprising:

at least one microelectrode insertable into said body tissue;

wherein said control circuitry is connected to said at least one microelectrode, and is configured to:

receive electrical signals recorded by said at least one microelectrode in said body tissue;

extract SPK signals and/or LFP signals from said received electrical signals;

measure at least one SPK parameter and/or at least one LFP parameter from said extracted SPK signals and/or said extracted LFP signals;

store in said memory said measured at least one SPK parameter and/or said at least one LFP parameter as said one or more indications.

Example 48. A system for determining a position of a lead inside a subject body, comprising:

an implantable lead insertable via an insertion trajectory through body tissue, comprising at least one macro electrode contact configured to record electrical signals from tissue surrounding said implantable lead;

a remote device, wherein said remote device stores one or more indications including a relation between a position in said body tissue and electrical measurements or indications thereof;

a control unit connectable to said implantable lead, comprising:

a communication circuitry configured to transmit and deliver signals to a remote device;

a user interface configured to generate a human detectable indication;

a control circuitry connected to said at least one macro electrode contact, wherein said control circuitry is configured to:

receive electrical signals recorded by said at least one macro-electrode contact;

process said received signals to obtain SPK signals and/or LFP signals;

signal said communication circuitry to transmit said SPK signals and/or said LFP signals to said remote device;

signal said user interface to generate said human detectable indication based on signals received from said remote device via said communication circuitry, wherein said received signals comprise at least one of information regarding the position of the lead and/or the position of said macro electrode contact in said body tissue, recommendations regarding at least one advancement parameter of said lead.

Example 49. A system according to example 48, wherein said remote device is configured to:
measure at least one SPK parameter and/or at least one LFP parameter from said obtained SPK signals and/or LFP signals;
determine a position of said lead and/or a position of said based on said stored indications and said measured at least one SPK parameter and/or said at least one LFP parameter;
transmit said signals to said communication circuitry, wherein said signals comprise at least one of said information regarding the position of the lead and/or the position of said macro electrode contact in said body tissue, said recommendations regarding at least one advancement parameter of said lead.

Example 50. A system according to any one of examples 48 or 49, wherein said remote device comprises at least one of a remote computer, a remote server, a remote cloud memory storage, a remote database.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as analyzing SPK and LFP signals, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1D is a schematic illustration of an electrode lead, for example a DBS lead, according to some exemplary embodiments of the invention;

FIG. 1E is a schematic illustration of a microelectrode, according to some exemplary embodiments of the invention;

FIG. 1F is a depiction of the user manually measuring the lead insertion depth;

FIG. 1G is a depiction of the system as described herewith;

FIG. 1H is a flow chart of a process for navigating a stimulating lead inside the brain, according to some exemplary embodiments of the invention;

FIG. 4B is a schematic illustration of processed SPK readings from 4 DBS lead contacts and processed SPK readings from microelectrodes, measured at 7 different depth locations, according to some embodiments of the invention.

DESCRIPTION OF SPECIFIC EMBODIMENTS OF THE INVENTION

Figure 1A:
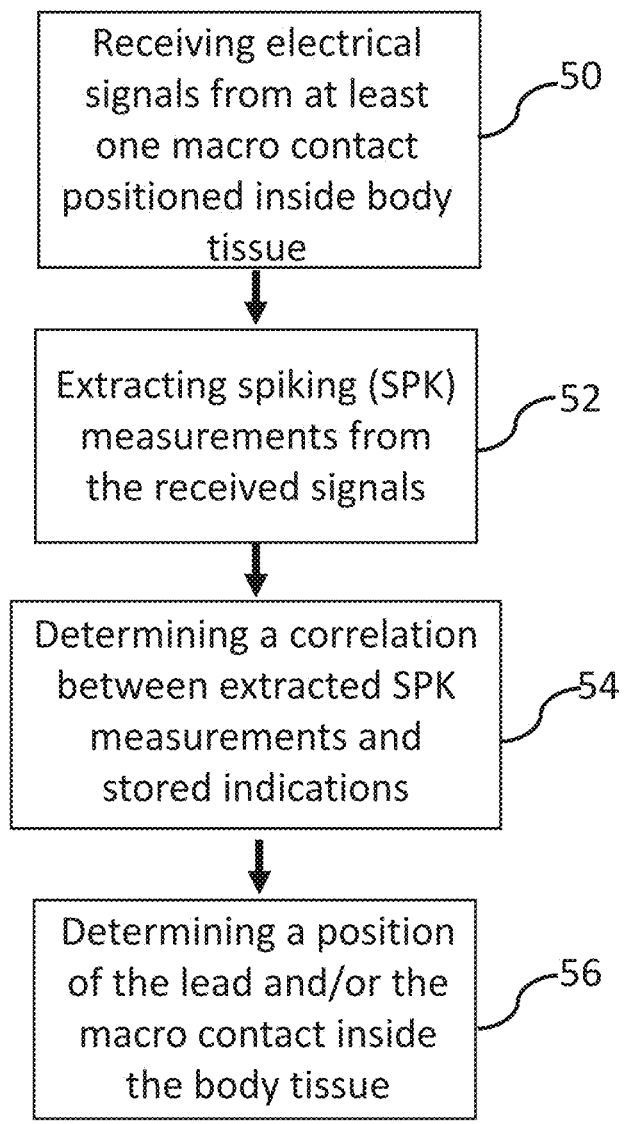
FIG. 1A is a flow chart of a process for determining a position of an electrode lead and/or a position of a macro electrode contact of the lead inside the body, according to some exemplary embodiments of the invention.

The present invention, in some embodiments thereof, relates to a navigation lead and system and/or parts thereof and, more particularly, but not exclusively, to methods of positioning a brain navigation lead comprising electrode contacts and configured to measure electrical activity of brain tissue.

An aspect of some embodiments relates to determining a position of a lead inside body tissue, by determining a correlation between lead measurements, for example spiking (SPK) measurements and/or local field potential (LFP) measurement, and indications stored in a memory. In some embodiments, two or more correlation values are calculated between the lead measurements and the stored indications, and the position of the lead is determined according to the highest correlation value. In some embodiments, the lead measurements are measurements measured from electrical signals recorded by the lead.

A potential advantage of using a correlation between SPK and/or LFP measurements from electrical signals recorded from a lead, and indications stored in a memory, may be to make unnecessary an insertion of a microelectrode into the body tissue, for example into the brain, prior to the insertion of the lead.

According to some embodiments, SPK measurements are measurements of spike activity. In some embodiments, SPK measurements are electrical signals measured from an extracellular space of a body tissue, for example brain tissue. In some embodiments, SPK measurements are measured from and/or indicate an activity level, for example an electrical activity level, of 1-1000 cells, for example 1-50 cells, 1-100 cells, 10-100 cells or any intermediate, smaller or larger range of cell number.

According to some embodiments, LFP measurements are measurements of an electric potential recorded in the extracellular space of a body tissue, for example brain tissue. In some embodiments, LFP measurements indicate an activity, for example an electrical activity of cells in a volume of at least 1 μm³, for example at least 5 μm³, at least 10 μm³, at least 20 μm³, at least 50 μm³, or any intermediate, smaller or larger volume.

According to some exemplary embodiments, the SPK measurements and/or the LFP measurements are measured from electrical signals recorded by at least one macro electrode contact, for example at least one macro contact of the lead. Alternatively or additionally, the SPK measurements and/or the LFP measurements are measured from electrical signals recorded by at least one microelectrode contact, for example micro contact of the lead.

According to some embodiments, a microelectrode contact, for example a micro contact, has a shape of a tip or a point. In some embodiments, the micro contact has a length or a diameter in a range of 1-100 μm, for example 1-20 μm, 10-50 μm, 20-80 μm, 40-100 μm or any intermediate, smaller or larger range of values. In some embodiments, the micro contact has an impedance in a range of 100-2000 Kohm at 1 KHz, for example 100-500 Kohm at 1 KHz, 200-1500 Kohm at 1 KHz, 200-1000 Kohm at 1 KHz or any intermediate, smaller or larger range of impedance values.

According to some embodiments, a macro electrode contact, for example a macro contact has a shape of a cylinder or an arc. In some embodiments, an axial length of a macro contact is in a range of 0.1-10 mm, for example 0.5-1.5 mm, 0.5-3 mm, 2-5 mm or any intermediate, smaller or larger range of values. In some embodiments, a diameter of the macro contact or a diameter of a cylindrical cross section of the macro contact is in a range of 0.1-5 mm, for example 0.2-1 mm, 0.4-1.3 mm or any intermediate, smaller or larger range of values. In some embodiments, an impedance of a macro contact is smaller than 200 Kohm at 1 KHz, for example smaller than 150 Kohm at 1 KHz, smaller than 100 Kohm at 1 KHz, smaller than 50 Kohm at 1 KHz, or any intermediate, smaller or larger impedance value.

According to some embodiments, the indications stored in the memory comprise indications of SPK measurements and/or LFP measurements, measured from electrical signals recorded by at least one microelectrode. In some embodiments, the electrical signals are recorded from at least one microelectrode contact, for example at least one micro contact of the electrode. Alternatively or additionally, the recorded signals are recorded from at least one macro electrode contact of the microelectrode.

Alternatively or additionally, the stored indications comprise SPK measurements and/or LFP measurements, measured from electrical signals recorded by at least one different lead.

According to some embodiments, the stored indications are based on measurements from at least one microelectrode and/or at least one lead retracted from the body tissue, for example from the brain.

According to some embodiments, SPK measurements comprise measurements of at least one SPK parameter, for example power spectrum density (PSD), Amplitude, Power, Frequency, Spike detection, Audio, Area under the curve, root mean square (RMS) and firing rate. In some embodiments, the calculated SPK parameter values comprise normalized values, averaged values.

According to some embodiments, LFP measurements comprise measurements of at least one LFP parameter, for example PSD, Amplitude, Power, Frequency, Spike detection, Audio, Area under the curve, Root mean square (RMS) and/or firing rate. In some embodiments, the LFP parameters are described in PCT application WO2018008034A2, incorporated herein as a reference in its entirely.

According to some embodiments, SPK signals are measured from a macro contact, by recording electrical signals from the macro contact in a high sampling rate, for example a sampling rate of at least 15 Kilo hertz (KHz), at least 20 KHz, at least 25 KHz, at least 30 KHz or any intermediate, smaller or larger sampling rate. In some embodiments, the recorded signals are then filtered to obtain electrical signals with a frequency in a range of 300-6000 Hz, for example 300-1000 Hz, 500-2000 Hz, 1500-6000 Hz or any intermediate, smaller or larger range of values. In some embodiments, a waveform is reconstructed from the SPK signals, for example using a full wave rectification algorithm. In some embodiments, at least one SPK parameter is measured using the reconstructed waveform.

According to some embodiments, a waveform from SPK data, for example SPK signals using a machine learning system. In some embodiments, in the machine learning process, we measure SPK data from lead electrical signals from many subject and/or from many body tissues or locations in a subject, with reference information from a microelectrode. In some embodiments, a machine learning system is programmed to match the recorded SPK data and the reference information.

According to some embodiments, the determined position of the lead, comprises a determined position of at least one contact on the lead, for example a position of at least one macro contact or a position of at least one micro contact. In some embodiments, the determined position is a determined relative position, for example a position which is relative to at least one location along an insertion trajectory of the lead, relative to at least one position in the body tissue, for example in the brain, relative to an entry site of the lead into the body tissue, for example into the bran or into the skull.

An aspect of some embodiments relates to determining a position of a lead inside a body, for example into the brain, based on similarity between SPK signals recorded by one or more electrode contacts on the lead, for example macro-electrode contacts, and stored indications. In some embodiments, the lead is used for delivery of an electric field to the body, for example by one or more macro-electrode contacts on the lead.

According to some embodiments, the stored indications comprise patient-specific indications, for example indications of SPK signals measured in the same patient into which a lead is inserted. In some embodiments, the SPK signals measured by at least one microelectrode. In some embodiments, the at least one microelectrode records the SPK signals prior to insertion of the lead into the body. In some embodiments, the at least one microelectrode records the SPK signals along a planned insertion trajectory of the lead. Alternatively, the at least one microelectrode contact records the SPK along an insertion trajectory that is different from a planned trajectory, and the stored indication are related to SPK measurements along a planned insertion trajectory that are predicted based on the recorded SPK signals. In some embodiments, the at least one microelectrode is removed from the body prior to insertion of the lead.

According to some exemplary embodiments, the stored indications comprise indications, which are based on SPK signals recorded from one or more different subjects.

According to some exemplary embodiments, the stored indications, for example the user-specific indications and/or the general indications indicate a correlation between previously measured SPK signals and a specific anatomical location. In some embodiments, the stored indications are in the form of an algorithm, a formula, and/or a lookup table, for example to allow conversion of electrical signals, for example SPK signals measured from a lead, for example a DBS lead, into a specific anatomical location.

An aspect of some embodiments relates to determining a position of a lead inside the brain based on SPK signals. In some embodiments, the lead includes at least one of a macro contacts and a micro contacts. In some embodiments, the SPK signals are measured or are filtered from signals measured by at least one of macro contacts and micro contacts of the lead or a microelectrode.

According to some embodiments, a similarity measure between the SPK signals measured by the lead and SPK signals measured by microelectrode is calculated, for example, after several steps of signal processing applied to each set of SPK signals. Alternatively or additionally, a similarity measure between SPK signals measured by the macro electrode contacts and processed LFP signals measured by the Microelectrode is calculated. Further alternatively or additionally, a similarity measure between processed LFP signals measured by the macro electrode contacts and processed SPK signals measured by the microelectrode is calculated. Yet further alternatively or additionally, a similarity measure between processed LFP signals measured by the macro electrode contacts and processed LFP signals measured by the microelectrode is performed.

According to some embodiments, an optimal target position, for example a target for delivery of a DBS stimulation is determined based on the calculated similarity measures, for example based on finding the position with the highest similarity between the processed SPK signals measured from the lead and the processed SPK signals measured by the microelectrode. In some embodiments, a target for delivery of a DBS stimulation is determined based on the similarity measures between indications derived from the signals recorded by the DBS lead and predefined, stored indications. In some embodiments, the predefined indications include at least one of indications derived from signals measured along multiple trajectories within the same patient or signals measured in multiple patients. In some embodiments, signals measured from the lead's macro contact and micro contacts are used for lead position verification or calibration of measured signal.

According to some embodiments, the similarity measure values being calculated can be selected from a wide range of known measures. A very commonly used measure is the correlation measure, yet many others are widely known and calculation formulae are readily available.

According to some embodiments, SPK measurements from a lead, which include SPK signals and/or measurements of at least one SPK parameter or indications thereof, are termed LEAD SPK. In some embodiments, the LEAD SPK is stored in a memory of the navigation system and/or in a remote device, for example a remote server, a cloud memory storage, a remote database.

According to some embodiments, LFP measurements from a lead, which include LFP signals and/or measurements of at least one LFP parameter or indications thereof, are termed LEAD LFP. In some embodiments, the LEAD LFP is stored in a memory of the navigation system and/or in a remote device.

According to some embodiments, SPK measurements from a microelectrode, which include SPK signals and/or measurements of at least one SPK parameter or indications thereof, are termed MER SPK. In some embodiments, the MER SPK is stored in a memory of the navigation system and/or in a remote device. Optionally, the microelectrode comprises at least one macro electrode contact and at least one microelectrode contact. In some embodiments, SPK signals are measured from said at least one microelectrode contact and from said at least one macro electrode contact.

According to some embodiments, LFP measurements from a microelectrode, which include LFP signals and/or measurements of at least one LFP parameter or indications thereof, are termed MER LFP. In some embodiments, the MER LFP is stored in a memory of the navigation system and/or in a remote device. Optionally, the microelectrode comprises at least one macro electrode contact and/or at least one microelectrode contact. In some embodiments, LFP signals are measured from the at least one microelectrode contact and/or from the at least one macro electrode contact.

According to some embodiments, a testing process is performed on a patient, by performing multiple measurements of SPK and/or LFP data and generating multiple correlations between the measured data and the stored indication. In some embodiments, the best correlations, for example the correlations with a high correlation value are used during the navigation of the lead. In some embodiments, correlations are compared and/or are combined for example over at least 1 mm, for example at least 2 mm, at least 10 mm of the insertion trajectory of the lead.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Lead Positioning

Reference is now made to FIG. 1A, depicting a process for determining a position of an electrodes lead and/or a position of a macro contact of the lead inside a body, according to some exemplary embodiments of the invention.

According to some exemplary embodiments, electrical signals are received from at least one macro electrode contact positioned in a body, at block 50. In some embodiments, the at least one macro electrode contact is positioned on an electrode lead inserted into the body, for example into the brain of a patient. In some embodiments, the received electrical signals are recorded in a high sampling rate, for example a sampling rate of at least 15 Kilo hertz (KHz), at least 20 KHz, at least 25 KHz, at least 30 KHz or any intermediate, smaller or larger sampling rate.

According to some exemplary embodiments, spiking (SPK) measurements are extracted from the received electrical signals at block 52. In some embodiments, extraction of SPK measurements comprises processing of the received signals. In some embodiments, the processing comprises filtering of the received electrical signals to get SPK-related signals. Additionally, the processing comprises calculating values of one or more SPK parameters from the SPK-related signals, for example using one or more algorithms, for example a wave rectification algorithm In some embodiments, the SPK parameters comprise power spectrum density (PSD), Amplitude, Power, Frequency, Spike detection, Audio, Area under the curve, root mean square (RMS) and firing rate. In some embodiments, the calculated SPK parameter values comprise normalized values, averaged values.

According to some exemplary embodiments, a level of correlation between the SPK measurements and one or more stored indications, is determined at block 54. In some embodiments, correlation between the SPK measurements and the stored indications is calculated at block 54. In some embodiments, the stored indications comprise indications of correlation between previously measured SPK parameters and anatomical locations inside the body, for example inside the brain. In some embodiments, the stored indications comprise indications of SPK parameters previously measured in the same patient, for example by at least one macro electrode contact and/or at least one microelectrode. Additionally or alternatively, the indications comprise indications of SPK measurements measured in one or more different patients. In some embodiments, the stored indications are in a form of a lookup table or an algorithm linking between SPK measurements and an anatomical location inside the body.

According to some exemplary embodiments, a position inside the body of the electrode lead and/or a position of the at least one macro electrode contact recording the electrical signals, is determined at block 56. In some embodiments, the position is determined based on the correlation determined at block 54. In some embodiments, the position is determined based on the correlation value calculated at block 54. In some embodiments, if the correlation between the SPK measurements and the stored indications is higher than 65%, for example higher than 70%, higher than 80%, higher than 85%, higher than 90%, higher than 95% or any intermediate, smaller or larger percentage value, a determined position is considered to be a valid position.

According to some exemplary embodiments, extracted SPK measurements, for example extracted SPK measurements associated with valid anatomical locations are used to update the stored indications. In some embodiments, the extracted SPK measurements, for example extracted SPK measurements associated with valid anatomical locations are used to update the stored algorithm or the stored lookup table associating SPK measurements with anatomical positions inside the body.

According to some exemplary embodiments, at least one indication, for example a human detectable indication is delivered with regard to at least one of determined correlation, calculated correlation value, and determined position. Alternatively or additionally, the at least one indication comprises recommendations regarding navigation of the electrode lead and or macro electrode contact inside the body.

Figure 1B:
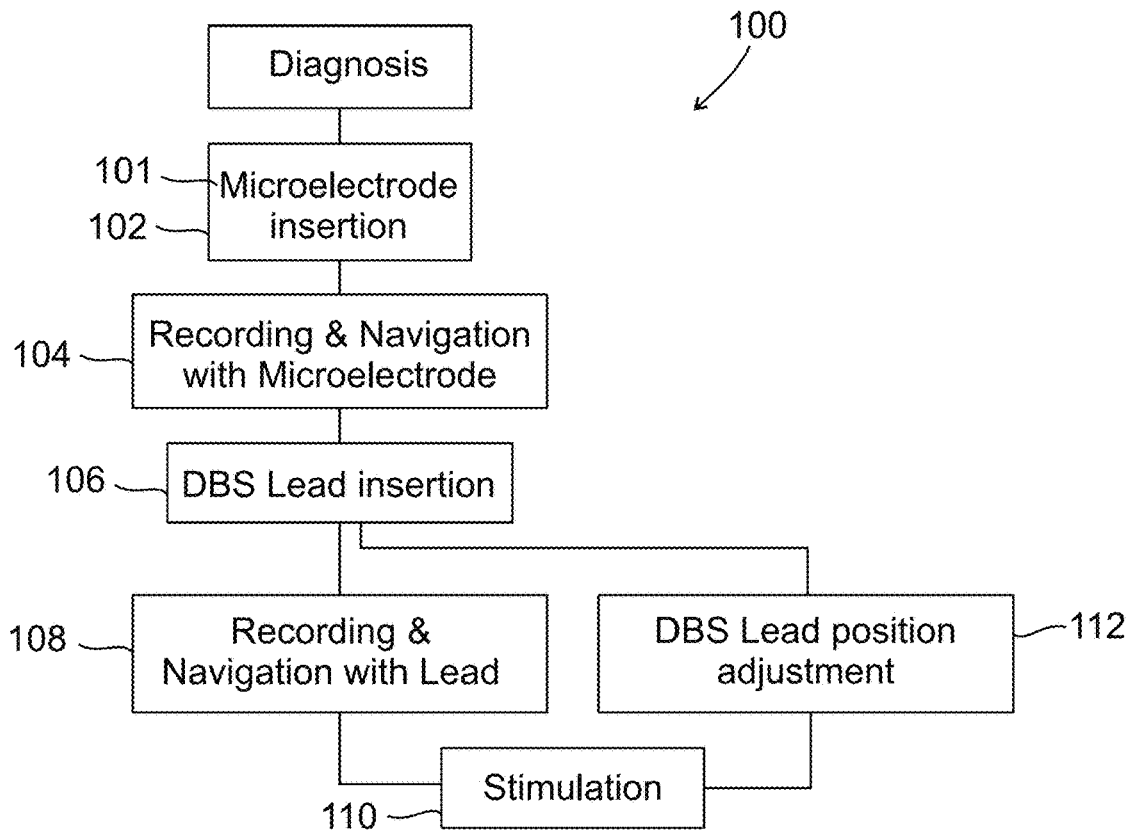
FIG. 1B is a flowchart of a Lead positioning procedure, according to some embodiments of the invention.
Figure 1B:
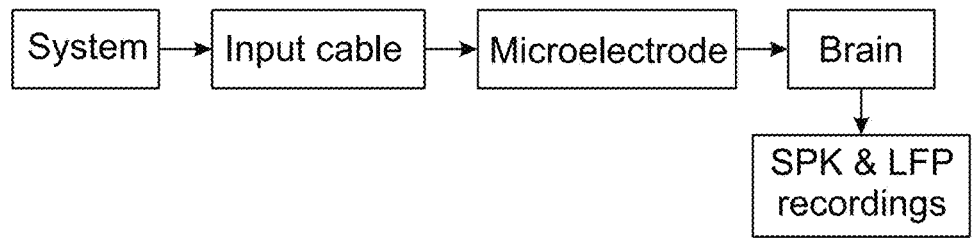
Figure 1B:
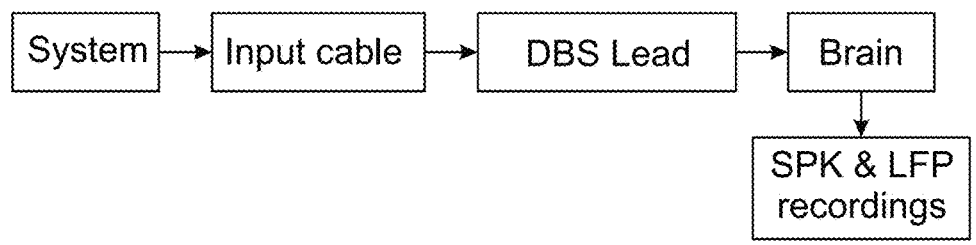

Reference is now made to FIG. 1B, depicting a lead positioning process, according to some exemplary embodiments of the invention.

According to some exemplary embodiments, a lead positioning process, for example a stimulating lead positioning process is based on signals recorded from one or more macro electrode contacts and/or one or more microelectrodes. In some embodiments, at least 2 electrodes are used in the stimulating lead positioning process, for example a Microelectrode is used to determine desired depth of insertion to reach predetermined target, and a Lead including at least one Macro contact to be implanted in the predetermined target.

According to some exemplary embodiments, a DBS procedure, for example DBS procedure 100 is initiated with a step of Microelectrode 101 insertion at block 102. In some embodiments, during microelectrode insertion 102, an insertion step size is in a range of 0.1-1 mm, for example 0.1-0.4 mm, 0.3-0.7 mm, 0.5-1 mm or any intermediate, smaller or larger step size. In some embodiments, the insertion is not performed in separate individual steps, but rather the microelectrode is continually driven into the tissue while signals are simultaneously recorded. In some embodiments, the velocity of insertion may be in the range of 50-1000 microns/sec, for example in the range of 50-200 microns/sec, in the range of 100-500 microns/sec, in the range of 100-300 microns/sec, in the range of 400-800 microns/sec, in the range of 500-800 microns/sec, in the range of 600-1000 microns/sec or any intermediate, smaller or larger range of values. In some embodiments, the microelectrode is inserted until reaching a predetermined target. In some embodiments, the target is predetermined prior to or during the insertion of the microelectrode.

According to some exemplary embodiments, the target is determined based on signals recorded at different depth locations along an insertion path, for example an insertion trajectory. In some embodiments, the recorded signals, comprise one or more spiking parameters, for example spiking pattern, spiking shape, oscillations in spike rate or any other spiking parameter. In some embodiments, each neuronal type exhibits spikes with typical characteristics, such as the duration of the spike from initiation to complete decay, which may vary from 0.2 milliseconds to about 1 millisecond, such as the degree of periodicity in the inter-spike interval, and the average firing rate of spikes, which varies at about 1-200 spikes/sec. In some embodiments, an expert identifies the neuronal type to which a recorded series of spikes is related, optionally using a computer program or an algorithm that identifies a correlation between spiking parameters and know patterns of spiking parameter associated with a specific neuronal type or a specific anatomical location. In some embodiments, as neuronal types are located in typical regions or nuclei in the brain, identifying the neuronal type provides information regarding the location in the brain.

According to some exemplary embodiments, another type of information present in SPK data is the level of the "background activity". In some embodiments, background activity appears as a "noise band" on the amplitude vs. time display of the SPK signals, and is optionally caused by spikes that are too weak in the recording to be individually recognized, yet accumulate to a band of activity around the 0 uV line that creates a band on the display. In some embodiments, some nuclei, such as the subthalamic nucleus (STN), has large background activity in the awake patient, while other nuclei have medium levels of background activity or low levels of background activity. In some embodiments, regions outside nuclei, namely white-matter regions, have very low background activity, and sporadic spiking activity at most.

According to some exemplary embodiments, an expert, for example an electrophysiologist, identifies the target based on the one or more spiking patterns, for example using a computer program or an algorithm that identifies a correlation between recorded spiking patters and one or more spiking patterns related indications stored in a memory. Optionally, the one or more spiking patterns are combined with the background activity. Alternatively or additionally, the target is determined using an automatic navigation system, for example as described in U.S. Pat. No. 8,792,972B2 and/or US20190069797A1, incorporated herein (as a reference) in its entirety. In some embodiments, the target is determined, for example using the automatic navigation system, based on applying machine learning methods to the spike signals recorded from one or more full trajectories.

According to some exemplary embodiments, in both cases, whether based on an expert or an automatic navigation system, one or more microelectrodes are advanced by a manual or electrically controlled drive on a trajectory in the brain, recording at a sequence of positions along the trajectory. In some embodiments, the recording at each position is analyzed, either by the expert or by the automatic navigation system, in order to, for example, estimate the current physiological position, and optionally to re-evaluate the sequence of previous physiological position estimates. In some embodiments, the advancement of the electrode is terminated either when the target nucleus or region has been fully mapped and there is no benefit in mapping additional depths, and/or when the expert or automatic system determines an optimal position has been reached. Alternatively or additionally, the advancement of the electrode is terminated due to another reason, for example unsatisfactory results indicating a faulty trajectory, patient related issues, or others).

According to some exemplary embodiments, when the electrode advancement is terminated, the obtained sequence of estimated physiological positions is reviewed, for example to determine which position would be optimal for placing the stimulating lead. In some embodiments, the sequence of recording positions may be real, corresponding to a sequence of steps in which the electrode is moved. Alternatively, the sequence of readings steps is virtual, and while the electrode is moved continually, without stopping at specific sites, data from nearby depths are bundled and analyzed, for example as if they were recorded at a single position that is the center of the nearby depths range.

According to some exemplary embodiments, following the insertion at block 102, recording and navigation from one or more microelectrodes 101 at block 104 is performed. In some embodiments, SPK signals are recorded from the one or more microelectrodes. In some embodiments, the navigation is performed based on the SPK recordings. In some embodiments, to validate the position, a Neurosurgeon who performs the procedure performs stimulation testing from a Macro contact optionally positioned on the microelectrode device, for example in order to observe reduction in symptom severity and/or emergence of stimulation side effects.

According to some exemplary embodiments, optionally after validating a position, the Neurosurgeon extracts the Microelectrode 101 and inserts a DBS lead 113 into the tissue at block 106. In some embodiments, the DBS lead is inserted in a similar insertion path as the insertion path of the microelectrode. Optionally, the DBS lead is inserted to the optimal position based on the previous Microelectrode recording and optional stimulation testing. In some embodiments, the optimal position is such that one of the stimulating lead macro contacts is positioned around the same insertion depth at which optimal recording results and/or optimal stimulation testing results were obtained.

According to some exemplary embodiments, the lead is positioned in a way that accounts for the existence of multiple contacts, for example to enable largest flexibility in future programing or tuning of the stimulation parameters. As an example, when implanting an electrode in the STN of a patient with Parkinson's Disease (PD), it may be considered optimal to have at least 2 contacts in the area known as the maximal "motor area", or "dorso-lateral oscillatory region" (DLOR) of the STN, for example, because stimulation of the DLOR is known to cause reduction in motor symptoms of PD. Optionally, if 2 contacts are positioned within the DLOR, then in post-operative DBS programing sessions and/or along the projected course of continued disease progression, there would be a choice of at least 2 contacts that have good prospects to provide beneficial stimulation treatment to the patient. In some embodiments, having more than one electrode contact in a stimulation target region allows, for example, flexibility, and for personal fitting of the actually used contact in face of specific symptom alleviated by various stimulation configurations and/or specific side effects that may appear. In some embodiments, the navigation phase in this example would aim to determine where the DLOR boundaries are, and/or the optimal position according to this embodiment is such that at least 2 of the lead macro contacts are positioned within these boundaries.

According to some exemplary embodiments, signals are recorded by one or more macro electrode contacts during recording and navigation of the DBS lead at block 108. In some embodiments, the signals comprise SPK signals. In some embodiments, the signals comprise both SPK and LFP signals. The recorded signals are processed to derive indications, and these indications are compared with indications derived from signals recorded from the microelectrode at block 104. In some embodiments, the processing includes at least one of filtering, full-wave-rectification, subtraction of an average of the signal and calculating power spectral density estimates. In some embodiments, the comparison of indications derived from lead signals and indications derived from microelectrode signals comprises calculation of similarity measures. According to some exemplary embodiments, once the DBS lead, for example one or more stimulating electrodes or stimulating electrode contacts are at a predetermined target, stimulation, for example an electrical stimulation is delivered to tissue surrounding the stimulating electrodes or stimulating electrode contacts at block 110. In some embodiments, the stimulation is performed as described at PCT/IL2017/050328, U.S. Pat. No. 8,792,972B2, and US20190069797A1.

According to some exemplary embodiments, an effect of the stimulation is determined, for example, a physiological effect is determined following the stimulation at block 110. In some embodiments, if the observed effect is not a desired effect, then the position of the DBS lead is adjusted at block 112. Following position adjustment at block 112, signals may be recorded from the lead, processed to derive indications that are compared with microelectrode-derived indications, as in block 108, to verify an optimal position or to determine another position adjustment for improving optimality.

According to some exemplary embodiments, for example in an alternative route, a DBS lead is inserted and navigated directly to a target site. In some embodiments, the DBS lead is inserted and navigated to the target by measuring SPK from one or more macro contacts on the lead, for example by two or more, three or more, four or more, macro contacts on the lead. In some embodiments, the measured SPK signals are processed to derive indications. In some embodiments, the derived indications are compared to one or more stored indications derived from SPK signals (similar to processing and comparison described above). In some embodiments, once the DBS lead is inserted into a desired target, for example when a target site is determined based on the comparison between the measured SPK signals and the stored indications, stimulation is provided, for example as described at block 110.

According to some exemplary embodiments, for example in the process described in FIG. 1B, the data, for example, the signals recorded from the DBS Lead 113, is RAW in frequencies in a range of 0.07-9000 Hz, for example 0.07-1 Hz, 0.5-100 Hz, 50-1000 Hz, 800-5000 Hz, 3000-9000 Hz or any intermediate, smaller or larger range of frequencies. In some embodiments, the RAW data, is filtered into two or more components, for example SPK and LFP. In some embodiments, a Lead LFP data has a 0.5-44 Khz sampling rate and a frequency in a range of 0.07-300 Hz, for example 0.07-100 Hz, 10-200 Hz, 100-300 Hz or any intermediate, smaller or larger range of frequencies. In some embodiments, the lead LFP data is filtered from the RAW data using a 0.07-300 Hz filter.

According to some exemplary embodiments, a Lead SPK data has a 10-44 Khz sampling rate and a frequency in a range of 300-6000 Hz, for example 300-1000 Hz, 500-2000 Hz, 1500-6000 Hz or any intermediate, smaller or larger range of values.

Exemplary System

Figure 1C:
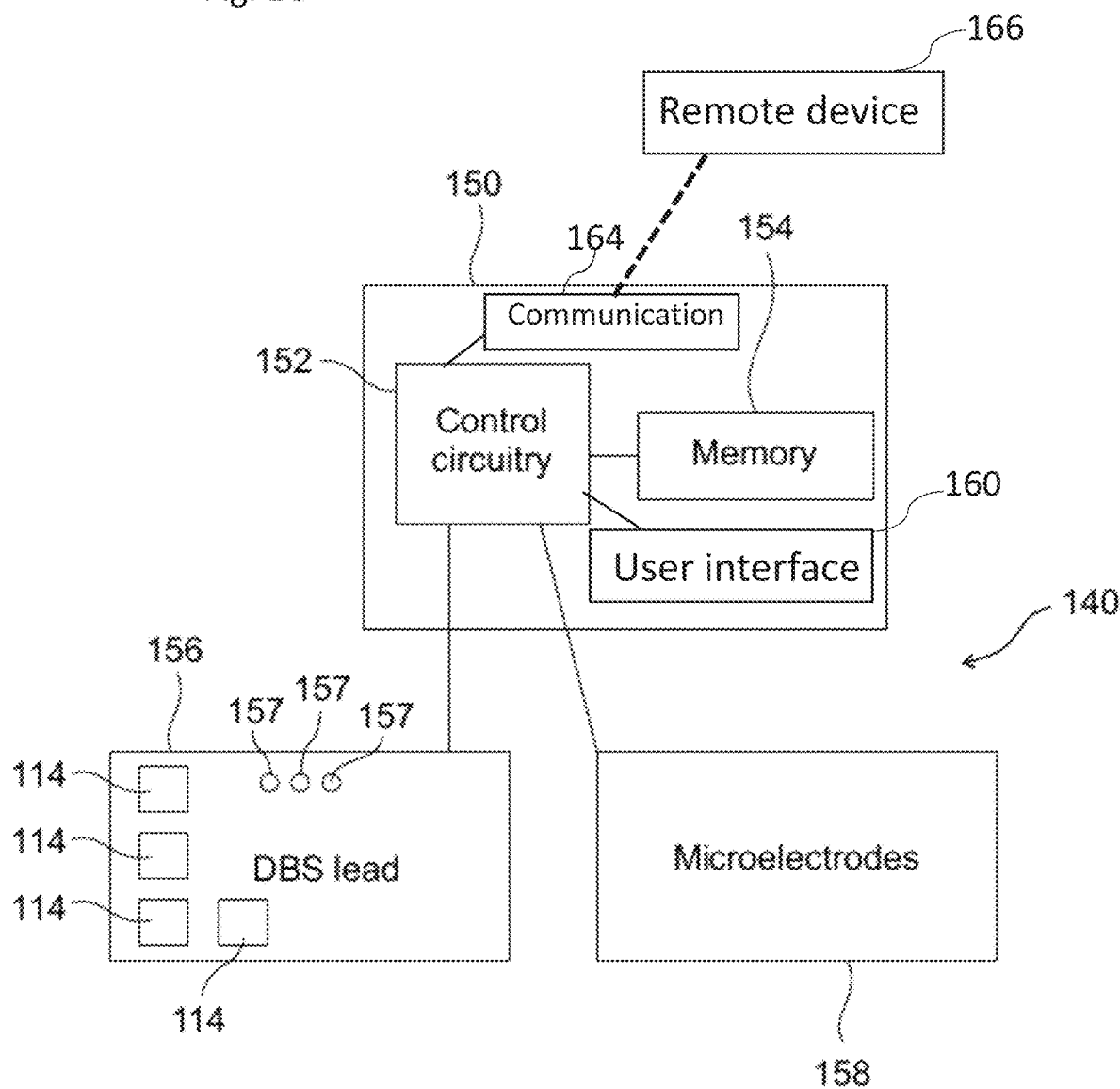
FIG. 1C is a block diagram of a system for brain navigation lead positioning, according to some exemplary embodiments of the invention.

Reference is now made to FIGS. 1C and 1G, depicting a brain navigation lead positioning system, according to some exemplary embodiments of the invention.

According to some exemplary embodiments, a brain navigation lead positioning system, for example system 140 comprises a computer medium, for example control unit 152. In some embodiments, the control unit 152 comprises a control circuitry 152 and a memory 154 electrically connected to the control circuitry 152.

According to some exemplary embodiments, the system 140 comprises an implantable electrode lead, for example a DBS lead, for example a DBS lead 156, electrically connected to the control circuitry 152. Alternatively, the control system is connectable to an implantable electrode lead, for example, DBS lead 156. In some embodiments, the DBS lead comprises one or more macro electrode contacts and/or one or more microelectrodes. In some embodiments, the DBS lead is shaped as a needle. In some embodiments, at least one microelectrode of the lead is positioned distally to the macro electrode contacts, for example closer to the distal tip of the lead.

According to some exemplary embodiments, the DBS lead is shaped and sized to penetrate into deep regions of the brain, for example regions located at a distance of more than 1 mm, for example more than 2 mm, more than 3 mm, more than 5 mm or any intermediate, smaller or larger value, from the upper external surface of the brain.

According to some exemplary embodiments, the one or more macro electrode contacts and/or one or more microelectrodes on the DBS lead are configured to measure SPK signals from body tissue, for example brain tissue surrounding the lead, for example the DBS lead. In some embodiments, SPK signals are electric signals having a frequency in a range of 300-6000 Hz, for example 300-1000 Hz, 500-2000 Hz, 1500-6000 Hz or any intermediate, smaller or larger range of values. Additionally or alternatively, the one or more macro electrode contacts and/or one or more microelectrodes on the DBS lead are configured to measure LFP signals. In some embodiments, one or more macro electrode contacts of the DBS lead are configured to deliver stimulation to brain tissue, for example electric field stimulation.

According to some exemplary embodiments, the system 140 comprises one or more brain insertable microelectrodes, for example microelectrodes 158. In some embodiments, the microelectrodes 158 are configured to measure SPK signals. In some embodiments, the system 140 is connectable to the one or more microelectrodes 158.

According to some exemplary embodiments, the control circuitry 152 is configured to measure electrical signals from the DBS lead 156 and/or from the one or more microelectrodes 158. In some embodiments, the measured electrical signals are stored in memory 154. In some embodiments, the memory comprises one or more algorithms, and/or look up tables for analysis of the stored signals. In some embodiments, the one or more algorithms and/or lookup tables are used to determine a correlation between recorded signals and stored indications, for example indications related to SPK signals and parameters thereof and/or anatomical positions. In some embodiments, indications derived from the recorded signals are stored in the memory, potentially saving memory by reducing the signal with typically more than 100,000 samples into 1, 2 or as much as 10 indications, that require 10,000-fold less memory to store.

According to some exemplary embodiments, the control circuitry 152 is configured to perform one or more of: obtaining readings from at least one of said microelectrodes 158 and/or the DBS lead 156, for example during advancement of at least one of said microelectrode and said implantable lead into the brain; applying one or more signal processing steps to the readings; comparing the readings; calculating similarity measures between the readings; determining location of the implantable lead based on the similarity measure; and providing recommendations based on the location determining.

According to some exemplary embodiments, the control circuitry 152 is configured to isolate SPK electrical signals from the signals measured by the DBS lead 156 and/or the microelectrodes 158 by applying a filter, optionally stored in memory 154, in a range of 300-6000 Hz. Alternatively or additionally, the control circuitry is configured to isolate LFP electrical signals from the signals measured by the DBS lead 156 and/or the microelectrodes 158 by applying a filter, optionally stored in memory 154, in a range of 0.07-300 HZ.

According to some exemplary embodiments, the control circuitry 152 is configured to apply one or more of the following signal processing steps to the recorded signals: filtering, full-wave-rectification, subtraction of an average of the signal and calculating a power spectral density estimate.

According to some exemplary embodiments, the control circuitry 152 is configured to measure at least one parameter of the SPK signal, for example by applying an algorithm or a formula stored in memory 154. In some embodiments, the at least one parameter comprises PSD, normalized PSD, Amplitude, Power, Frequency, Spike detection, Audio, Area under the curve, root mean square (RMS) and firing rate. In some embodiments, the calculated SPK parameter values comprise normalized values, averaged values.

According to some exemplary embodiments, the control circuitry 152 is configured to measure at least one parameter of the LFP signal, for example by applying an algorithm or a formula stored in memory 154. In some embodiments, the at least one parameter comprises PSD, Amplitude, Power, Frequency, Spike detection, Audio, Area under the curve, Root mean square (RMS) and/or firing rate. In some embodiments, the LFP parameters are described in PCT application WO2018008034A2. In some embodiments, the calculated LFP parameter values comprise normalized values, averaged values.

According to some exemplary embodiments, the memory 154 comprises information which includes at least one of SPK measurements, LFP measurements, values of at least one SPK parameter, values of at least one LFP parameter, and/or indications thereof. In some embodiments, the information stored in the memory 154 is measured from electrical signals recorded by at least one of the microelectrodes 158, for example at least one microelectrode that was inserted into the body tissue, for example into the brain, prior to the insertion of the DBS lead. Alternatively or additionally, the information stored in the memory 154 is measured from electrical signals recorded by one or more of the microelectrodes, for example microelectrodes 157 of the lead, for example the DBS lead 156.

According to some exemplary embodiments, at least some of the information stored in the memory is stored in a remote device 166, for example a remote server, a cloud memory storage, a remote database. In some embodiments, the information stored in the memory and/or in the remote device is in a form of an algorithm, a formula, and/or lookup table, for example indicating a relation between measured LFP parameters and/or measured SPK parameters and an anatomical location, a position inside a body tissue, and/or a relative position in the body tissue.

According to some exemplary embodiments, the control circuitry is configured to compare or determine a correlation between LFP and SPK signals filtered from the measured signals, and/or measurements of LFP and/or SPK parameters and information stored in the memory 154 or in the database. In some embodiments, the control circuitry determines a highest similarity measure between the filtered SPK and LFP signals. In some exemplary embodiments, the control circuitry is configured to compare between LFP or SPK signals recorded from the lead and LFP or SPK signals recorded from the microelectrode. In some exemplary embodiments, the control circuitry is configured to compare signals after one or more steps of signal processing have been applied to them. In some exemplary embodiments, the control circuitry is configured to compare signals by calculating similarity measures between pairs of signals. In some exemplary embodiments, the similarity measures are correlation measures, cross correlation measures, positive definite kernels such as the Radial Basis Function, cosine similarities, or similarities based on inverting distance metrics, such as the inverse of the Euclidean distance or the Manhattan distance between to measurement vectors.

According to some exemplary embodiments, the control circuitry 152 is configured to receive electrical signals from the DBS lead 156. In some embodiments, the received electrical signals are signals recorded by at least macro electrode contact of the lead, for example, macro electrode contact 114. Alternatively or additionally, the received electrical signals are signals recorded by at least one microelectrode of the lead, for example microelectrode 157. Optionally, the at least one microelectrode 157 is located distally on the lead body to the position of the at least one macro electrode contact. In some embodiments, the received electrical signals are signals recorded in a high sampling rate. In some embodiments, the sampling rate is in a range of 10 KHz-60 KHz, for example 15 KHz-30 KHz, 20 KHz-50 KHz or any intermediate, smaller or larger range of sampling rate. In some embodiments, the received electrical signals are recorded in a frequency range of 0.5 Hz-10,000 Hz, for example 1 Hz-5000 Hz, 1000 Hz-6000 Hz, 3000 Hz-6000 Hz, 4000 Hz-8000 Hz, or any intermediate, smaller or larger range of frequencies.

According to some exemplary embodiments, the control circuitry 152 is configured to extract LFP signals from the received electrical signals. In some embodiments, the control circuitry 152 filters the received electrical signals to obtain LFP electrical signals with a frequency of up to 500 Hz, for example up to 400 Hz, up to 300 Hz or any intermediate, smaller or larger frequency value. Alternatively, the control circuitry 152 filters the received electrical signals to obtain LFP electrical signals in a frequency range of 0.5-500 Hz, for example 0.5 Hz-200 Hz, 1 Hz-300 Hz, 100 Hz-300 Hz or any intermediate, smaller or larger range of frequencies. In some embodiments, the control circuitry filters the received electrical signals to obtain LFP signals using a filter, for example a filter stored in the memory 154.

According to some exemplary embodiments, filtering of the received signals to obtain SPK and/or LFP signals is performed in the remote device 166.

According to some exemplary embodiments, the control circuitry 152 is configured to measure values of at least one parameter of the SPK signals, for example PSD. In some embodiments, the control circuitry is configured to measure PSD by applying at least one algorithm stored in the memory 154, for example a full wave rectification algorithm. In some embodiments the measured at least one parameter, for example PSD, or indications thereof is stored in the memory 154. Alternatively, the measurements of the at least one SPK parameter are performed in the remote device 166. In some embodiments, the measured at least one parameter, for example PSD, or indications thereof is stored in the database.

According to some exemplary embodiments, the control circuitry 152 is configured to measure values of at least one parameter of the LFP signals, for example PSD. In some embodiments, the control circuitry is configured to measure PSD by applying at least one algorithm stored in the memory 154. In some embodiments the measured at least one parameter, for example PSD, or indications thereof is stored in the memory 154. Alternatively, the measurements of the at least one LFP parameter are performed in the remote device 166. In some embodiments, the measured at least one parameter, for example PSD, or indications thereof is stored in the database.

According to some exemplary embodiments, the control circuitry 152 is configured to extract SPK signals and/or LFP signals for electrical signals received from at least one microelectrode, for example one of the microelectrodes 158. In some embodiments, the SPK signals and/or the LFP signals are extracted as described with respect to the electrical signals received from the lead. In some embodiments, the control circuitry 152 is configured to measure at least one SPK parameter and/or at least one LFP parameter from the extracted signals, for example as described above with respect to the electrical signals received from the lead. In some embodiments, the SPK and/or LFP signals extracted from the microelectrode or indications thereof are stored in the memory 154 and/or in a remote device 166. Alternatively or additionally, the measured parameters of the SPK and/or LFP signals from the microelectrode or indications thereof are stored in the memory 154 or in the remote device 166.

As used herein SPK measurements from a lead, for example DBS lead 156, which include SPK signals and/or measurements of at least one SPK parameter or indications thereof, are termed LEAD SPK. In some embodiments, the LEAD SPK is stored in the memory 154 and/or in a remote device 166.

As used herein LFP measurements from a lead, for example DBS lead 156, which include LFP signals and/or measurements of at least one LFP parameter or indications thereof, are termed LEAS LFP. In some embodiments, the LEAD LFP is stored in the memory 154 and/or in a remote device 166.

As used herein SPK measurements from a microelectrode, for example microelectrode 158, which include SPK signals and/or measurements of at least one SPK parameter or indications thereof, are termed MER SPK. In some embodiments, the MER SPK is stored in the memory 154 and/or in a remote device 166.

As used herein LFP measurements from a microelectrode, for example microelectrode 158, which include LFP signals and/or measurements of at least one LFP parameter or indications thereof, are termed MER LFP. In some embodiments, the MER LFP is stored in the memory 154 and/or in a remote device 166.

According to some exemplary embodiments, the control circuitry 152 is configured to determine a position or a relative of a lead 156 and/or the position or a relative position of at least one macro electrode contact of the lead 156 using indications stored in the memory 154 and at least one of the LEAD LFP and LEAD SPK. In some embodiments, the stored indications comprise MER LFP and/or MER SPK. Optionally, the stored indications comprise LEAD LFP and/or LEAD SPK measured from a lead different than lead 156.

According to some exemplary embodiments, the control circuitry 152 is configured to calculate a correlation between at least one of LEAD SPK and MER SPK, LEAD LFP and MER LFP, LEAD SPK and MER LFP, and LEAD LFP and MER SPK. In some embodiments, the correlation between at least one of LEAD SPK and MER SPK, LEAD LFP and MER LFP, LEAD SPK and MER LFP, and LEAD LFP and MER SP, is performed in a remote device 166.

According to some exemplary embodiments, the correlation is performed between measurements of SPK and/or LFP from an electrode lead currently positioned inside the body tissue and/or currently advanced through the body tissue, and SPK and/or LFP measurements from at least one microelectrode previously positioned in the body tissue, for example a microelectrode located distally to the macro electrode contact on the same lead, or a microelectrode that was retracted from the body tissue prior to the insertion and advancement of the lead.

According to some exemplary embodiments, the control circuitry 152 is configured to determine a position or relative position of the lead and/or of at least one macro electrode contact of the lead based on the correlation with the highest correlation value. Alternatively, a remote device 166 determines a position or a relative position of the lead and/or of at least one macro electrode contact of the lead based on the correlation with the highest correlation value.

According to some exemplary embodiments, a control unit 150 of the system 140, comprises the control circuitry 152 and the memory 154. In some embodiments, the control circuitry is connectable to the lead 156 and/or to one or more microelectrodes 158.

According to some exemplary embodiments, the control unit 150 comprises a user interface 160, configured to deliver human detectable indications, for example audio and/or visual indication to a user of the system 140. In some embodiments, the user interface 160 comprises a display.

According to some exemplary embodiments, the control unit 150 signals the user interface 160 to deliver an indication, for example to a user of the system 140. In some embodiments, the indication comprises information regarding the determined position or the determined relative position of the lead or a macro electrode contact of the lead inside the body tissue, for example inside the brain. In some embodiments, the indication comprises recommendation regarding at least one parameter of the lead advancement through the body tissue. In some embodiments, the at least one advancement parameter comprises advancement speed, advancement direction, advancement step size, and advancement termination. In some embodiments, the recommendations are generated by the remote device 166 and are transmitted to the control unit 150. In some embodiments, the control circuitry 152 is configured to signal the user interface 160 to deliver an indication with the received recommendations or a processed form of the received recommendations, for example to a user of the system 140.

According to some exemplary embodiments, the recommendations provided by the control circuitry, for example via the user interface 160, comprise Go/No Go output and/or degree of advancement output. According to some exemplary embodiments, the Go/No Go output indicates to the user whether to change the lead position along insertion trajectory. According to some exemplary embodiments, the degree of advancement output indicates to the user at least one of amount of steps to take to further advance the lead, direction of further advancement of the lead, for example insert or extract, length of advancement in units of length, for example millimeters or inches. For example, the instruction will read "insert the lead 1 mm further" or "extract the lead by 2 steps" or any other combination thereof.

According to some exemplary embodiments, the indications derived from signals readings measured by the DBS lead 156 at least one of macro electrode contacts 114 and micro electrode contacts 157 and/or from the microelectrodes 158 are compared to indications previously collected from other two or more subjects, and optionally from one or more insertion trajectories in these subjects. In some embodiments, control circuitry 152 is configured to at least one of calculating in one or more steps a relation between said SPK and LFP components and location along the trajectory or calculating in one or more steps a relation between said SPK and LFP components and optimal implantation target.

According to some exemplary embodiments, the calculation of the relation is the result of a machine learning process. In some embodiments, in the machine learning process, an algorithm has been fed as input the SPK and/or LFP components of a signal, or indications derived from processing SPK and/or LFP signals recorded in at least two patients, paired with "ground truth" data regarding location of the lead along the trajectory or degree of outcome optimality, and through a sequence of algorithmic steps the algorithm provides as an output the method of calculating the relation between the inputs and the ground truth. In some embodiments, the ground truth data fed to the algorithm is based on post-operative imaging scans, for example CT scans, from which an accurate position of the lead along the trajectory can be deduced. Alternatively or additionally, the ground truth data fed to the algorithm may is based on clinical outcomes of the DBS procedure, for example, as can be evaluated by a clinical rating scale such as the Unified Parkinson's Disease Rating Scale (UPDRS). In some embodiments, in this case the optimal position "ground truth" is based on these clinical findings.

In some embodiments, the control circuitry is configured to provide at least semi-automatic or automatic navigation to a target, for example by determining a correlation between signals recorded from the lead and one or more indication stored in a memory, for example a remote device 166. In some embodiments, the remote device 166 comprises remote storage, a remote server, a remote cloud memory. As used herein, the term remote relates to a location outside a room in which the lead navigation and/or implantation is performed. In some embodiments, the navigation is based on the results of calculating the relation between SPK or LFP signals, or indication derived thereof, and the optimal position or the position in the trajectory.

According to some exemplary embodiments, the control unit 150 comprises a communication circuitry 164. In some embodiments, the communication circuitry is configured to transmit and/or receive signals, for example wireless signals to and/or from the remote device, for example remote device 166. In some embodiments, the communication circuitry is configured to transmit and/or receive signals to and/or from a remote computer or a remote cellular device. Optionally, the communication circuitry 164 is configured to communicate, for example via wireless signals, with a lead, for example a DBS lead and/or with at least one microelectrode.

According to some embodiments, the navigation system, for example system 140 is used for automatic navigation of a lead, for example a DBS lead through a body tissue, for example the brain towards a desired anatomical target. In some embodiments, in automatic navigation the control circuitry 152 controls an operation of a motor, for example a drive motor configured to move the lead, automatically, for example without receiving input from a user, according to determined position or the determined relative position of the lead. In some embodiments, in automatic navigation, the control circuitry 152 automatically controls a duration, direction and speed of the motor, according to the determined position of the lead. In some embodiments, in automatic navigation, the control circuitry 152 automatically controls a step size of the lead advancement, according to the determined position of the lead.

According to some embodiments, the navigation system, for example system 140 is used for semi-automatic navigation of a lead, for example a DBS lead through a body tissue, for example the brain towards a desired anatomical target. In some embodiments, in a semi-automatic navigation, the control circuitry signals the user interface 160 to generate and deliver recommendations to a user of the navigation system 140 according to the determined position of the lead. In some embodiments, the recommendations comprise recommendations regarding at least one parameter of the lead advancement and/or regarding the determined position of the lead. In some embodiments, in a semi-automatic navigation, the user needs to provide an input via the user interface with regard to the delivered indications. In some embodiments, the control circuitry controls the operation of the motor according to the input received from the user.

Exemplary Electrode Lead and Microelectrode

Reference is now made to FIG. 1D, depicting an electrode lead, for example a deep brain stimulation (DBS) lead, according to some exemplary embodiments of the invention. In some embodiments, the electrode lead is termed as "lead".

According to some exemplary embodiments, an electrode lead, for example electrode lead 131 is a DBS lead. In some embodiments, the lead 131 has an elongated body 137 having a longitudinal axis 139 and a distal tip 141. In some embodiments, the term distal as used herein refers to closer to a tissue through which a lead or a microelectrode penetrates. In some embodiments, the elongated body has a ration of at least 1:5, for example at least 1:7, at least 1:10 or any intermediate, smaller or larger ratio between a diameter of the body and the length of the body. In some embodiments, the distal tip 141 is shaped and sized to penetrate through body tissue, for example through the brain. Optionally, the distal tip 141 is a pointed tip. Optionally, the lead 131 comprises at least one microelectrode, for example a microelectrode contact at the distal tip 141 and/or proximal to the distal tip 141 along the body 137. In some embodiments, the external surface of the lead 131 is smooth. In some embodiments, the body of the lead is rigid. In some embodiments, the body of the lead is rigid in an axial direction and at least partly flexible in a lateral direction.

According to some exemplary embodiments, the lead 131 comprises at least one or at least two macro electrode contacts, for example macro contact 133 and macro contact 135 proximal, for example closer to an entry position into the body tissue, to the distal tip 141. In some embodiments, the at least two macro contacts are axially spaced apart along the body 137. In some embodiments, an axial distance between two macro contact of the lead is at least 0.2 mm, for example at least 0.4 mm, 0.5 mm, 1 mm, 5 mm, at least 10 mm or any intermediate, smaller or larger axial distance.

According to some exemplary embodiments, a lead comprises at least 2, 3, 4, 5, 6, 7 or any larger number of macro contacts. In some embodiments, at least some of the macro contacts are segmented macro contacts, for example are shaped as an arc, for example to provide direction stimulation towards a specific tissue volume or a specific tissue target.

According to some exemplary embodiments, the lead 131 is shaped as a needle. In some embodiments, the lead has a maximal outer diameter smaller than 20 mm, for example smaller than 10 mm, smaller than 5 mm, smaller than 3 mm or any intermediate, smaller or larger value.

According to some exemplary embodiments, a microelectrode contact, for example a micro contact, has a shape of a tip or a point. In some embodiments, the micro contact has a length or a diameter in a range of 1-100 μm, for example 1-20 μm, 10-50 μm, 20-80 μm, 40-100 μm or any intermediate, smaller or larger range of values. In some embodiments, the micro contact has an impedance in a range of 100-2000 Kilo Ohm (Kohm) at 1 KHz, for example 100-500 Kohm at 1 KHz, 200-1500 Kohm at 1 KHz, 200-1000 Kohm at 1 KHz or any intermediate, smaller or larger range of impedance values.

According to some exemplary embodiments, a macro electrode contact, for example a macro contact has a shape of a cylinder or an arc. In some embodiments, an axial length of a macro contact is in a range of 0.1-10 mm, for example 0.5-1.5 mm, 0.5-3 mm, 2-5 mm or any intermediate, smaller or larger range of values. In some embodiments, a diameter of the macro contact or a diameter of a cylindrical cross section of the macro contact is in a range of 0.1-5 mm, for example 0.2-1 mm, 0.4-1.3 mm or any intermediate, smaller or larger range of values. In some embodiments, an impedance of a macro contact is smaller than 200 Kohm at 1 KHz, for example smaller than 150 Kohm at 1 KHz, smaller than 100 Kohm at 1 KHz, smaller than 50 Kohm at 1 KHz, or any intermediate, smaller or larger impedance value.

According to some exemplary embodiments, SPK and/or LFP measurements are extracted from electrical signals recorded by at least one macro contact of the lead, for example lead 131. In some embodiments, if a lead comprises at least one micro contact, SPK and/or LFP measurements are extracted from electrical signals recorded by the at least one micro contact of the lead.

Reference is now made to FIG. 1E depicting a microelectrode, according to some exemplary embodiments of the invention.

According to some exemplary embodiments, a microelectrode, for example microelectrode 143 has an elongated body having a ratio of at least 1:5, for example at least 1:7, at least 1:10 or any intermediate smaller or larger ratio between a diameter of the body and a length of the body. In some embodiments, the microelectrode 143 has a longitudinal axis 145 and a distal tip 149. In some embodiments, the microelectrode 143 comprises at least one micro contact, at said distal tip 149. In some embodiments, the microelectrode 143 comprises at least one macro contact, for example macro contact 147 located proximally to said distal tip 149, along the microelectrode body. Optionally, the microelectrode, for example microelectrode 143 comprises two or more macro contacts, which are optionally axially spaced-apart.

According to some exemplary embodiments, SPK signals and/or LFP signals are extracted from electrical signals recorded by the at least one micro contact of the microelectrode, for example microelectrode 143.

According to some exemplary embodiments, SPK signals and/or LFP signals are extracted from electrical signals recorded by at least one macro contact of the microelectrode 143, for example macro contact 147.

Exemplary Navigation Process

Reference is now made to FIG. 1H depicting a navigation process of an electrode lead, for example a stimulating electrode lead inside the brain, according to some exemplary embodiments of the invention.

According to some exemplary embodiments, a subject is diagnosed at block 120. In some embodiments, the subject is diagnosed with a disease that requires insertion of an electrode into the body, for example to deliver an electric field to tissues of the body. In some embodiments, the delivery of the electric field to tissues of the body is part of a treatment for the disease. Alternatively, the delivery of the electric field to the tissues is part of a diagnosing process. In some embodiments, the disease comprises Parkinson's disease (PD), spinal cord injury, brain injury, dystonia genetic, dystonia non-genetic, Alzheimer's disease (AD), essential tremor, obesity, epilepsy, and pain.

According to some exemplary embodiments, the diagnosing at block 120 comprises performing at least one imaging of the body, for example the brain. In some embodiments, the imaging comprises at least one of magnetic resonance imaging (MRI), functional MRI, x-ray imaging, ultrasound imaging, computerized tomography (CT), and positron emission tomography (PET) scan. In some embodiments, the diagnosis comprises selecting an anatomical target for delivery of the electric field. In some embodiments, the anatomical target is selected according to the disease, and/or according to results of the imaging. Additionally, at least one insertion trajectory of an electrode lead into the body, for example into the brain is planned, for example based on the imaging results and the selected anatomical target. In some embodiments, for treating PD, the anatomical target comprises the subthalamic nucleus (STN), the Globus pallidus internus (GPi). In some embodiments, for treating Dystonia, the anatomical target is the GPi. In some embodiments, for treating essential tremor the anatomical target comprises the STN, the ventral intermediate nucleus of thalamus (VIM) and/or the posterior subthalamic area (PSA). In some embodiments, for treating Epilepsy, the anatomical target is the thalamus and/or the zona incerta.

According to some exemplary embodiments, at least one microelectrode is inserted into the body, for example into the brain at block 122. In some embodiments, the at least one microelectrode is inserted along the at least one planned trajectory towards the selected anatomical target. In some embodiments, during the insertion of the at least one micro electrode, electrical signals from tissue surrounding the at least one microelectrode are recorded. In some embodiments, the electrical signals are recorded along the insertion trajectory of the microelectrode towards the selected anatomical target.

According to some exemplary embodiments, spiking (SPK) parameters are measured at block 124. In some embodiments, the SPK parameters are measured from the recorded electrical signals. In some embodiments, SPK parameter values are calculated at block 124. In some embodiments, the SPK parameters comprise PSD, normalized PSD, Amplitude, Power, Frequency, Spike detection, Audio, Area under the curve, root mean square (RMS) and firing rate. In some embodiments, the calculated SPK parameter values comprise normalized values, averaged values. Alternatively, or additionally, LFP parameters are measured at block 124. In some embodiments, the LFP parameters are measured from the recorded electrical signals. In some embodiments, LFP parameter values are calculated at block 124. In some embodiments, the LFP parameters comprise PSD, Amplitude, Power, Frequency, Spike detection, Audio, Area under the curve, Root mean square (RMS) and/or firing rate.

According to some exemplary embodiments, the measured SPK parameters, for example indications of the measured SPK parameters, are stored in a memory, at block 126. In some embodiments, the stored indications comprise a relation between the measured SPK parameters and a specific anatomical location, for example an anatomical location inside the brain. In some embodiments, the indications are stored in a form of an algorithm or a lookup table correlating measured SPK parameters with an anatomical location inside the body. In some embodiments, the memory is a memory of a remote device. Alternatively, the memory is a memory of a navigation system, for example memory 154 shown in FIG. 1C.

Alternatively, or additionally, the measured LFP parameters, for example indications of the measured LFP parameters, are stored in a memory, at block 126. In some embodiments, the stored indications comprise a relation between the measured LFP parameters and a specific anatomical location, for example an anatomical location inside the brain. In some embodiments, the indications are stored in a form of a formula, an algorithm or a lookup table correlating measured LFP parameters with an anatomical location inside the body. In some embodiments, the memory is a memory of a remote device, for example remote device 166 shown in FIG. 1C. Alternatively, the memory is a memory of a navigation system, for example memory 154 shown in FIG. 1C.

According to some exemplary embodiments, the at least one microelectrode is removed from the body tissue, for example from the brain at block 128. In some embodiments, the at least one microelectrode is removed from the body, for example after reaching a desired anatomical target inside the brain, for example the selected anatomical target.

According to some exemplary embodiments, the at least one microelectrode is not removed from the body. In some embodiments, the at least one microelectrode is located on the same lead as at least one macro electrode contact used for stimulation and recording. Optionally, the at least one microelectrode is located distally, for example closer to a distal end of the lead, to the at least one macro electrode contact on the same lead.

According to some exemplary embodiments, at least one of the inserting at block 122, the measuring at block 124, the storing at block 126, and the removing at block 128 is performed on one or more different patients. In some embodiments, the indications stored at block 126 comprise results of a statistical processing of the SPK and/or LFP measurements obtained from the one or more different patient.

Alternatively, the inserting at block 122, the measuring at block 124, the storing at block 126, and the removing at block 128 are performed on the same patient into which the electrode lead is planned to be introduced, for example the patient diagnosed at block 120.

According to some exemplary embodiments, an electrode lead is introduced and is advanced into the brain of the diagnosed patient, at block 129. In some embodiments, the electrode lead comprises a DBS lead, used to deliver an electric field to brain tissue. In some embodiments, the lead comprises at least one macro electrode contact. Optionally, the lead comprises only macro electrode contacts. Alternatively, the lead comprises at least one macro electrode contact, and at least one microelectrode located distally to the at least one macro electrode contact, for example a microelectrode used for recording the electrical signals at block 122.

According to some exemplary embodiments, the lead is advanced to a desired target through the same insertion trajectory as the insertion trajectory of the microelectrode at block 122. Alternatively, the insertion trajectory of the lead is determined based on the target selected during diagnosis, and optionally based on stored optional trajectories. In some embodiments, the insertion trajectory of the lead is determined based on stored SPK indications per a potential insertion trajectory. In some embodiments, the lead is advanced through an insertion trajectory that is laterally distanced from the insertion trajectory of the microelectrode at block 122, in up to 20 mm, for example up to 15 mm, up to 10 mm or any intermediate, smaller or larger value.

According to some exemplary embodiments, electrical signals are recorded from at least one macro electrode contact of the lead at block 130. In some embodiments, electrical signals are recorded from two or more macro electrode contacts of the lead.

According to some exemplary embodiments, SPK parameters are measured from the recorded electrical signals at block 132. In some embodiments, values of the SPK parameters are calculated at block 132.

According to some exemplary embodiments and optionally, local field potential (LFP) parameters are measured from the recorded electrical signals at block 134. In some embodiments, values of the LFP parameters are calculated at block 132. In some embodiments, LFP parameters comprise Amplitude, Power, Frequency, Spike detection, Audio, Area under the curve, Root mean square (RMS) and/or firing rate. In some embodiments, the LFP parameters are described in PCT application WO2018008034A2.

According to some exemplary embodiments, a correlation between measured SPK parameters, measured at block 132 and stored indications, for example indications stored at block 126, is determined at block 136. In some embodiments, the correlation is determined as described at block 54 of FIG. 1A. In some embodiments, a correlation value between the measured SPK parameters and the stored indications is calculated at block 136. In some embodiments, the correlation is performed between LEAD SPK and MER SPK, and/or between LEAD SPK and MER LFP. In some embodiments, MER SPK and/or MER LFP are stored in the memory, for example as described at block 126.

According to some exemplary embodiments, a correlation between measured LFP parameters, measured at block 134, and the stored indications, for example indications stored at block 126, is optionally determined at block 138. In some embodiments, a correlation value between the measured LFP parameters and the stored indications is calculated at block 138. In some embodiments, the correlation is performed between LEAD LFP and MER SPK, and/or between the LEAD LFP and MER LFP. In some embodiments, MER SPK and/or MER LFP are stored in the memory, for example as described at block 126.

According to some exemplary embodiments, a correlation between measured SPK parameters combined with measured LFP parameters, and stored indications, for example indications stored at block 126, is determined at block 136.

According to some exemplary embodiments, a position of the lead inside the brain, for example a position of at least one macro electrode contact of the lead, is determined based on the determined correlation, at block 142. In some embodiments, the position of the lead is determined based on the correlation determined at block 136, and/or based on a correlation value calculated at block 136. Alternatively or additionally, the position of the lead is determined based on the correlation determined at block 138, and/or based on a correlation value calculated at block 138.

According to some exemplary embodiments, a position of the lead inside the body tissue, for example in the brain is determined by selecting a correlation with the highest correlation value. In some embodiments, the position of the lead inside the brain is determined by selecting a correlation with the highest value from at least one of a correlation between SPK measured by the lead (LEAD SPK) and stored indications, for example MER SPK and/or MER LFP, and a correlation between LFP parameters measured by the lead (LEAD LFP) and the stored indications.

Additionally or alternatively, the position of the lead is determined by selecting a correlation with a correlation value higher than 0.7 (70%), for example higher than 0.75, higher than 0.8, higher than 0.9 or any intermediate, smaller or larger value. In some embodiments, a position of the lead inside the brain comprises an anatomical location inside the brain. In some embodiments, the correlation value indicates a similarity level between the two compared features.

According to some exemplary embodiments, a validity level of a determined anatomical position is determined based on the correlation value. In some embodiments, if the correlation value is higher than 0.8 (80%), for example higher than 0.85, higher than 0.9 or any intermediate smaller or larger value, then the determined anatomical position is valid. In some embodiments, if the correlation value is smaller than 0.65 (65%), for example smaller than 0.6, smaller than 0.55 or any intermediate, smaller or larger value, then the determined anatomical position is not valid. In some embodiments, if the correlation value is in a range of 0.65 to 0.8, for example 0.65-0.75, 0.7-0.8 or any intermediate, smaller or larger range of values, then the determined anatomical position is a potential anatomical position.

According to some exemplary embodiments, the lead advancement is adjusted at block 144. In some embodiments, the lead advancement is adjusted based on the correlation value and/or the determined anatomical position. In some embodiments, if the determined anatomical position is the anatomical target selected at block 120, then the advancement is stopped. In some embodiments, if the determined anatomical position is the anatomical target selected at block 120, the lead is advanced or retracted until a selected one or macro electrode contacts configured to deliver an electric field to the tissue at the anatomical target is positioned at the anatomical target or in a desired distance from the anatomical target.

According to some exemplary embodiments, if the determined anatomical position is close to the anatomical target selected at block 120, for example located at a distance smaller than 20 mm from the anatomical target, for example smaller than 10 mm, smaller than 5 mm or any intermediate, smaller or larger distance from the anatomical target, the step size or the speed of the advancement lead is reduced. In some embodiments, if the determined anatomical position is distant from the anatomical target selected at block 120, for example located at a distance larger than 30 mm, for example larger than 35 mm, larger than 40 mm, larger than 45 mm or any intermediate, smaller or larger distance from the anatomical target, then the advancement step size or advancement speed of the lead is increased.

According to some exemplary embodiments, if the determined anatomical position is not a valid position, for example has a correlation value smaller than 0.75, then the step size of the lead advancement or the advancement speed is reduced, for example to allow measurements with higher resolution.

According to some exemplary embodiments, an indication, for example a human detectable indication is delivered at block 146. In some embodiments, the indication comprises information regarding at least one of, the determined correlation, the calculated correlation value, the determined position of the lead and/or the determined position of a macro contact electrode, and the distance between the determined position and the selected anatomical target. Additionally or alternatively, the indication is delivered to a user navigating the lead, and comprises at least one of, a suggested step size, a suggested advancement speed, instructions to change the step size of the lead, instructions to change advancement speed of the lead and instructions to stop the advancement of the lead.

According to some exemplary embodiments, the lead advancements is stopped at 148. In some embodiments, the lead advancement is stopped based on the position determined at block 142. In some embodiments, the lead advancement is stopped, for example when reaching the selected treatment target.

Exemplary Signals Processing

Figure 1I:
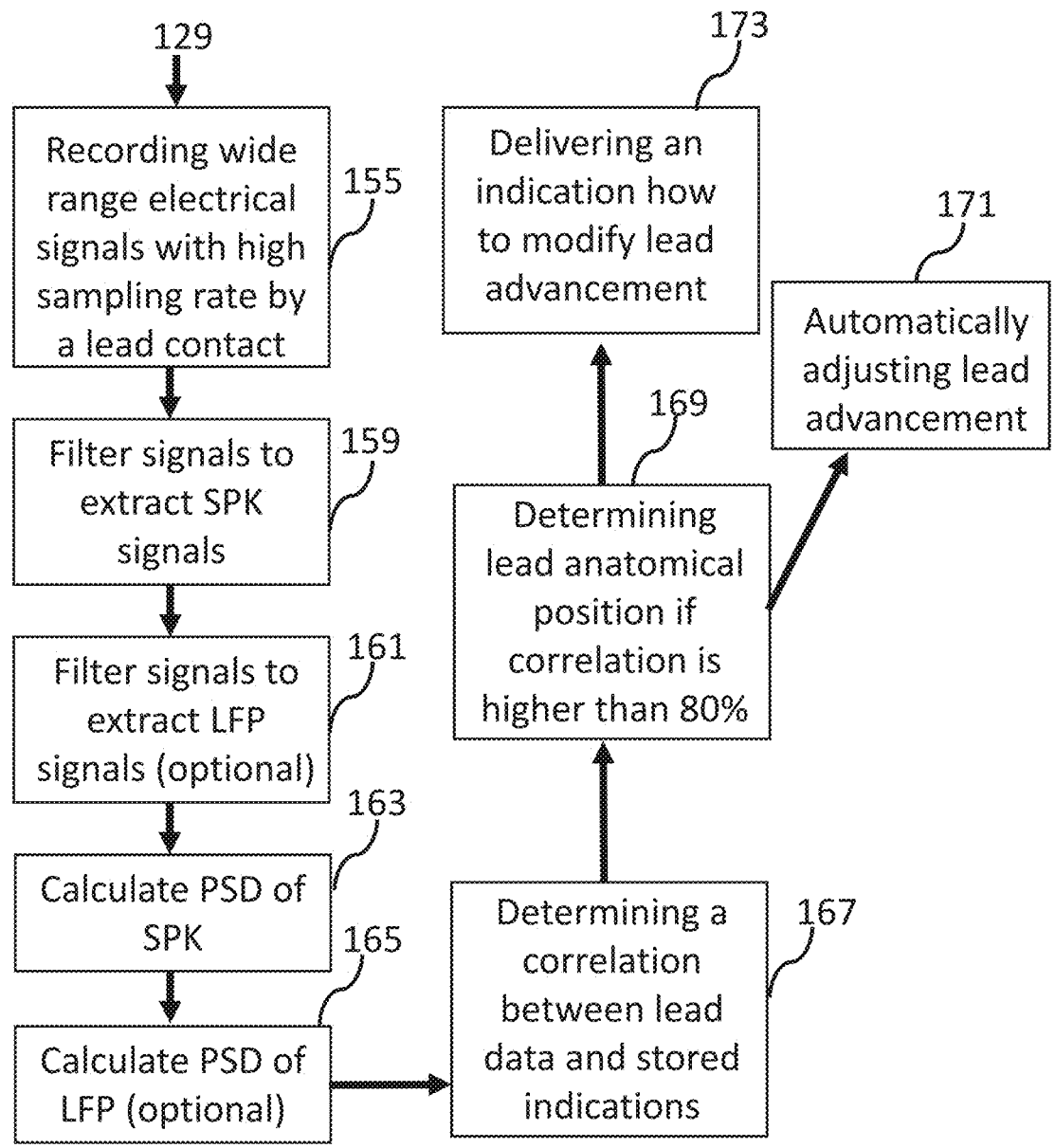
FIG. 1I is a flow chart of a processing method of electrical signals, according to some exemplary embodiments of the invention.

Reference is now made to FIG. 1I, depicting a processing method of the recorded electrical signals, according to some exemplary embodiments of the invention;

According to some exemplary embodiments, electrical signals are recorded by at least one electrode of a lead, for example a DBS lead, at block 155. In some embodiments, the electrical signals are recorded from one or more macro electrode contacts of the lead, for example by 1, 2, 3, 4, 5 or any number of macro electrode contacts of the lead. In some embodiments, the electrical signals in a frequency range of 1 Hz-10,000 Hz, for example 1 Hz-5000 Hz, 1000 Hz-6000 Hz, 3000 Hz-6000 Hz, 4000 Hz-8000 Hz, or any intermediate, smaller or larger range of frequencies, is recorded at block 155. Additionally, or alternatively, the electrical signals are recorded in a sampling rate in a range of 10 KHz-60 KHz, for example 15 KHz-30 KHz, 20 KHz-50 KHz or any intermediate, smaller or larger range of sampling rates.

According to some exemplary embodiments, the recorded signals are filtered to extract SPK related signals, at block 159. In some embodiments, the recorded electrical signals are filtered to extract SPK signals in the range of frequencies of 250 Hz-8000 Hz, for example 250 Hz-6500 Hz, 300 Hz-6000 Hz or any intermediate, smaller or larger range of frequencies.

According to some exemplary embodiments, the recorded electrical signals are filtered to extract LFP-related signals, at block 161. In some embodiments, the recorded electrical signals are filtered to extract LFP signals in the range of frequencies of 1 Hz-300 Hz, for example 1 Hz-200 Hz, 50 Hz-250 Hz or any intermediate, smaller or larger range of frequencies.

According to some exemplary embodiments, values of at least one SPK parameter are calculated at block 163, for example from the filtered SPK signals. In some embodiments, the at least one SPK parameter comprises Amplitude, Frequency, Peak of the power spectrum density graph, Curve of the power spectrum graph, and/or Area under the curve of power spectrum graph. In some embodiments, values of power spectrum density (PSD) of the SPK signals is calculated. In some embodiments, values of the at least one SPK parameter, for example the PSD, is calculated by applying a full wave rectification algorithm on the SPK signals.

According to some exemplary embodiments, values of at least one LFP parameter are calculated at block 165, for example from the filtered LFP signals. In some embodiments, the at least one LFP parameter comprises PSD, Amplitude, Frequency, Peak of the power spectrum density graph, Curve of the power spectrum graph, and/or Area under the curve of power spectrum graph. In some embodiments, values of PSD of the LFP signals are calculated. In some embodiments, values of the at least one LFP parameter, for example the PSD, is calculated, for example by filtering electrical signals to get LFP data in a frequency range of 0.07 Hz-300 Hz, for example 0.5-150 Hz, 50-200 Hz, 100-300 Hz or any intermediate, smaller or larger range of frequencies. In some embodiments, the filtered electrical signals are then subjected to a power spectrum density analysis.

According to some exemplary embodiments, a correlation between the signals recorded from the lead and stored indications is performed at block 167. In some embodiments, a correlation is performed between the calculated at least one SPK parameter, for example PSD with one or more stored indications, for example indications relating the at least one SPK parameter with a specific anatomical location inside the body, for example inside the brain. Alternatively or additionally, a correlation is performed between the calculated at least one LFP parameter, for example PSD with one or more stored indications, for example indications relating the at least one LFP parameter with a specific anatomical location inside the body, for example inside the brain.

According to some exemplary embodiments, the stored indications are indications relating at least one LFP parameter and/or at least one PSD parameter to a specific anatomical location. In some embodiments, a correlation is determined between the calculated at least one SPK parameter, and at least one stored LFP-related indication. Alternatively, or additionally, a correlation is determined between the calculated at least one LFP parameter and at least one stored SPK-related indication. In some embodiments, determining a correlation comprises calculating a correlation value indicating a level of correlation between data originating from the lead and the stored indications.

According to some exemplary embodiments, an anatomical position, for example a valid anatomical position of the lead inside the body, for example inside the brain, is determined at block 169. In some embodiments, an anatomical position, for example a valid anatomical position of an electrode contact of the lead, for example a macro electrode contact, is determined at block 169. In some embodiments, the anatomical position is valid if a correlation value is higher than 0.8 (80%), for example higher than 0.8. higher than 0.85, higher than 0.9 or any intermediate, smaller or larger value.

According to some exemplary embodiments, an indication is delivered to a user controlling the lead navigation at block 173. In some embodiments, the indication, for example a human detectable indication comprises information and/or suggestions how to adjust the advancement of the lead inside the brain according to the determined lead position.

Alternatively, the navigation system is automatically adjusting lead advancement parameters at block 171, according to the determined lead position or the determined position of at least one macro electrode contact of the lead.

Figure 1J:
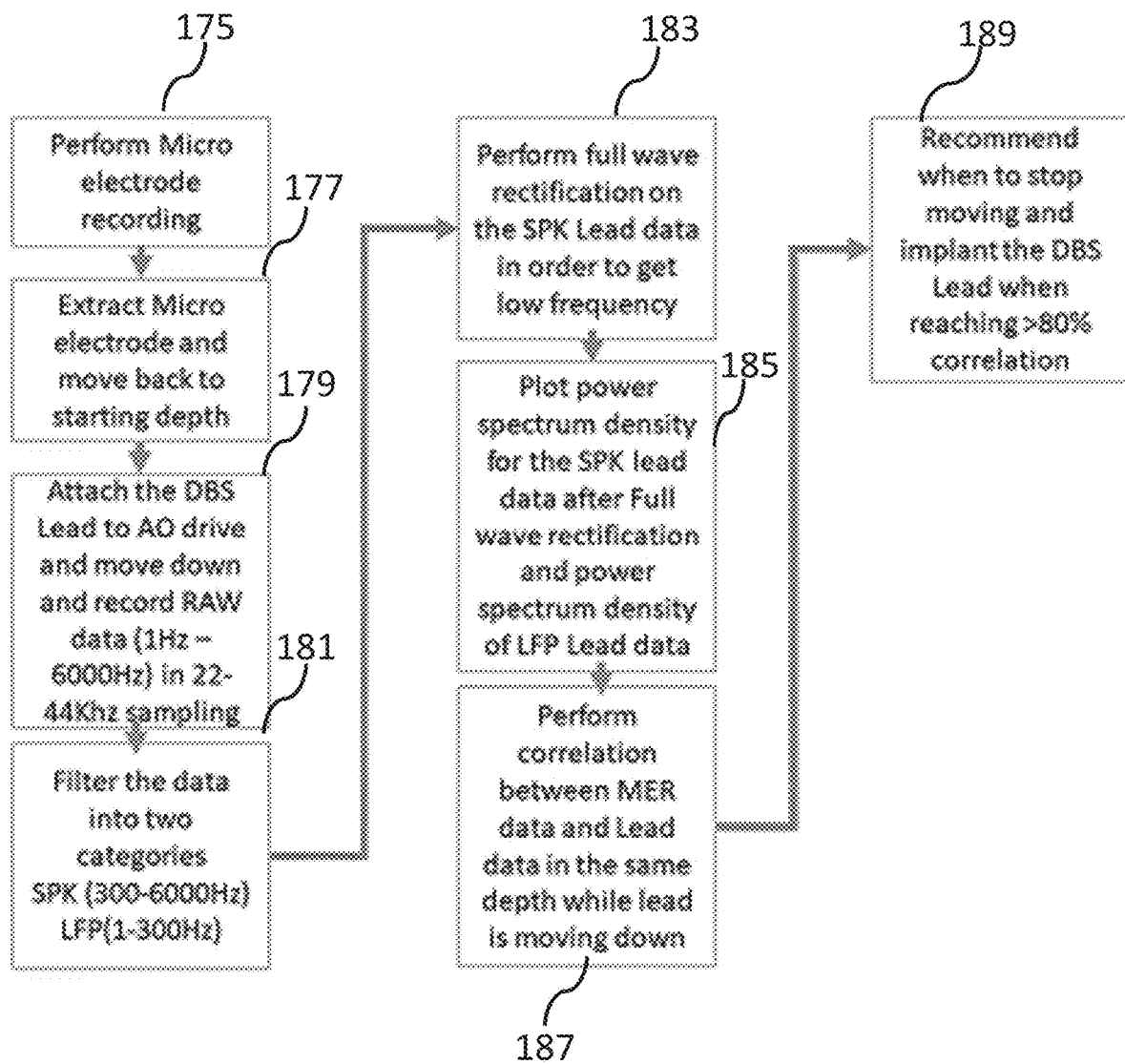
FIG. 1J is a flow chart of a detailed process for navigating a lead based on a correlation between data recorded from the lead and data recorded by at least one microelectrode, according to some exemplary embodiments of the invention.

Reference is now made to FIG. 1J, describing a detailed process for navigating a lead based on correlation between data recorded by the lead and data recorded by at least one microelectrode, for example microelectrode recording (MER), according to some exemplary embodiments of the invention.

According to some exemplary embodiments, microelectrode recording (MER) is performed at block 175. In some embodiments, the MER is performed by at least one microelectrode that is inserted into the body, for example into the brain. In some embodiments, the MER and/or parameter of the MER are stored in a memory. In some embodiments, the microelectrode is advanced towards a stimulation target inside the brain along an insertion trajectory. In some embodiments, the MER is recorded along the insertion trajectory.

According to some exemplary embodiments, the at least one microelectrode is extracted back, for example to a starting depth, at block 177.

According to some exemplary embodiments, a DBS lead is attached to a drive unit of a navigation system, and is moved down and records data, at block 179. In some embodiments, the DBS lead is moved along the insertion trajectory of the microelectrode. Alternatively, the DBS lead is moved along an insertion trajectory located at a distance of up to 10 mm, for example up to 8 mm, up to 5 mm or any intermediate, smaller or larger distance from the insertion trajectory of the microelectrode. In some embodiments, the signals recorded by the DBS lead are in a frequency range of 1 Hz-6000 Hz, for example 100 Hz-5000 Hz, 1000 Hz-6000 Hz or any intermediate, smaller, or larger range of values. In some embodiments, the signals are recorded with a high sampling rate in a range of 22 KHz-44 KHz, for example 22 KHz-30 KHz, 25 KHz-40 KHz or any intermediate, smaller, or larger range of values.

According to some exemplary embodiments, the recorded signals are filtered, at block 181. In some embodiments, the recorded signals are filtered into SPK signals, for example signals in a range of 300 Hz-6000 Hz, for example in a range of 500 Hz-5000 Hz, in a range of 1000 Hz-6000 Hz or any intermediate, smaller or larger range of frequencies. Additionally, the recorded signals are filtered into LFP signals, for example signals in a range of 1 Hz-300 Hz, for example in a range of 50 Hz-250 Hz, 100 Hz-300 Hz, 1 Hz-200 Hz or any intermediate, smaller, or larger range of frequencies.

According to some exemplary embodiments, low frequency signals are extracted from the SPK lead data, for example SPK lead signals, at block 183. In some embodiments, the low frequency signals are extracted by applying full wave rectification of the SPK lead data.

According to some exemplary embodiments, a plot of PSD for the SPK data based on the extracted low frequency signals, and of PSD of LFP lead data is generated at block 185.

According to some exemplary embodiments, a correlation is performed between the stored MER data, and the lead data at block 187. In some embodiments, the correlation is performed between the stored MER data, and the lead data for a similar depth, and optionally while the lead is advanced along the insertion trajectory.

According to some exemplary embodiments, a recommendation regarding the advancement of the lead is delivered at block 189. In some embodiments, the recommendation comprises when to stop the advancement of the lead, for example when reaching a desired stimulation target inside the brain. In some embodiments, a recommendation to stop the advancement of the lead and to fix the position of the DBS lead, for example to implant the DBS lead is delivered when a performed correlation has a correlation value higher than 80%, for example higher than 85%, higher than 90% or any intermediate, smaller or larger percentage value. Alternatively, the navigation system automatically controls the advancement of the lead and parameters thereof.

Exemplary Macro Contacts and Microelectrode Readings

Figure 2A:
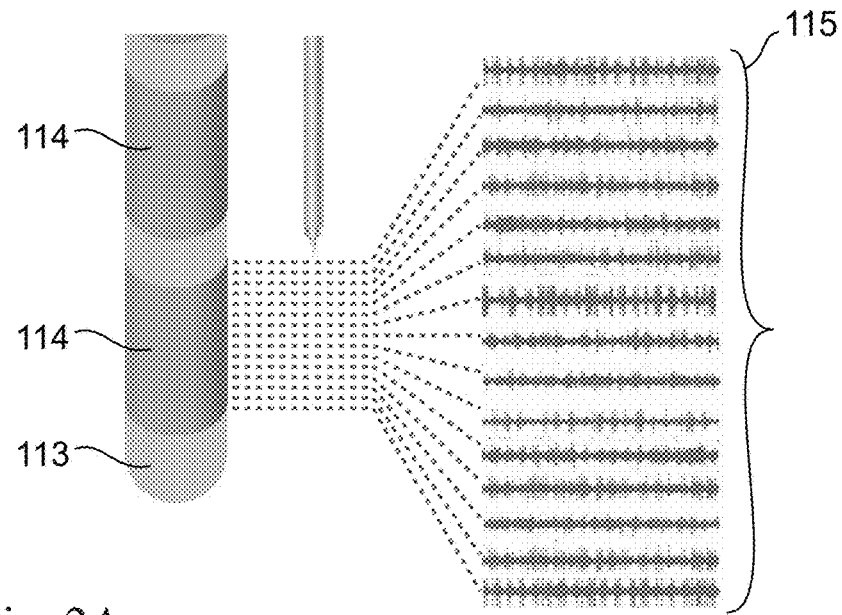
FIG. 2A is a schematic illustration of a stimulating Lead and Microelectrode positioning and readings, according to some embodiments of the invention.
Figure 2B:
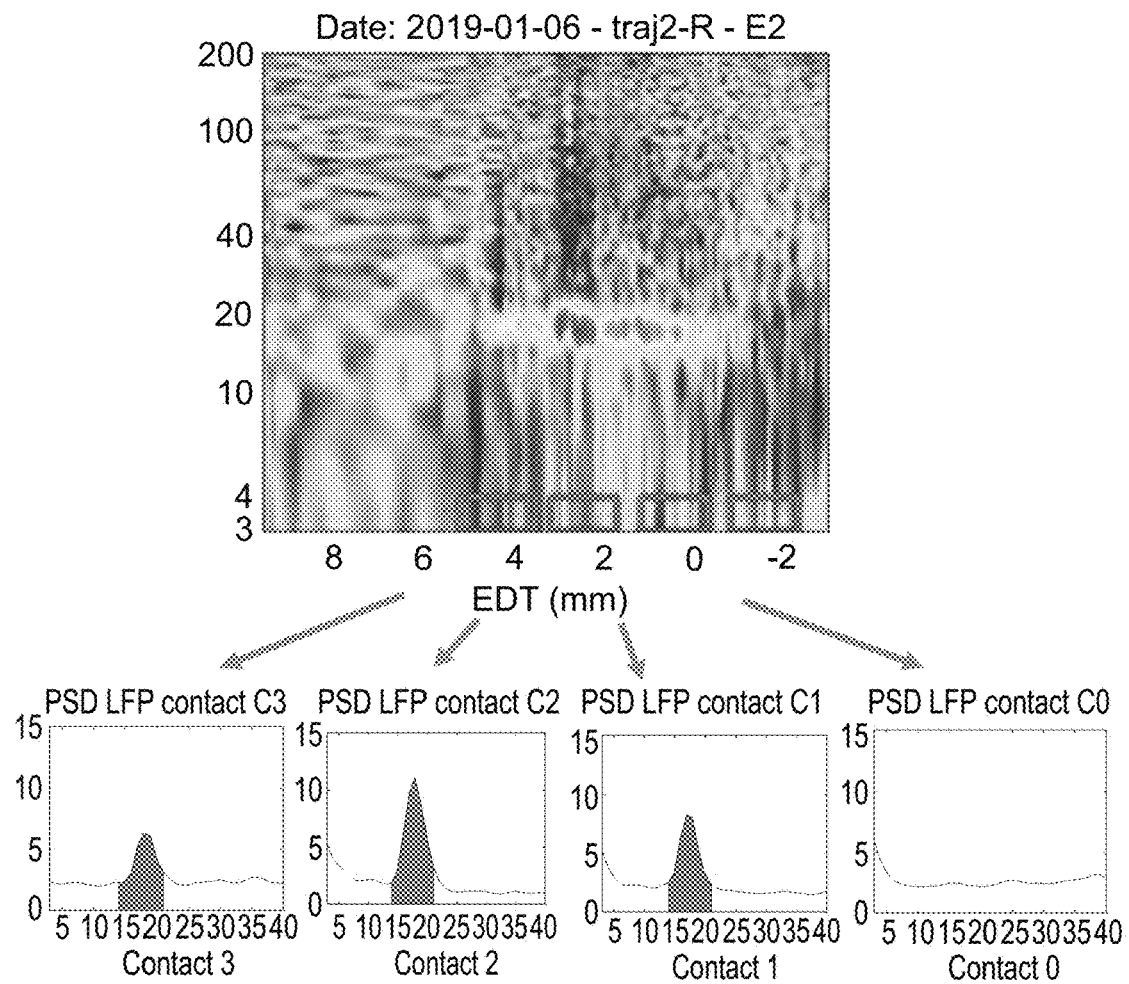
FIG. 2B which is an exemplary Average MER spiking activity at the DBS contact location
Figure 3:
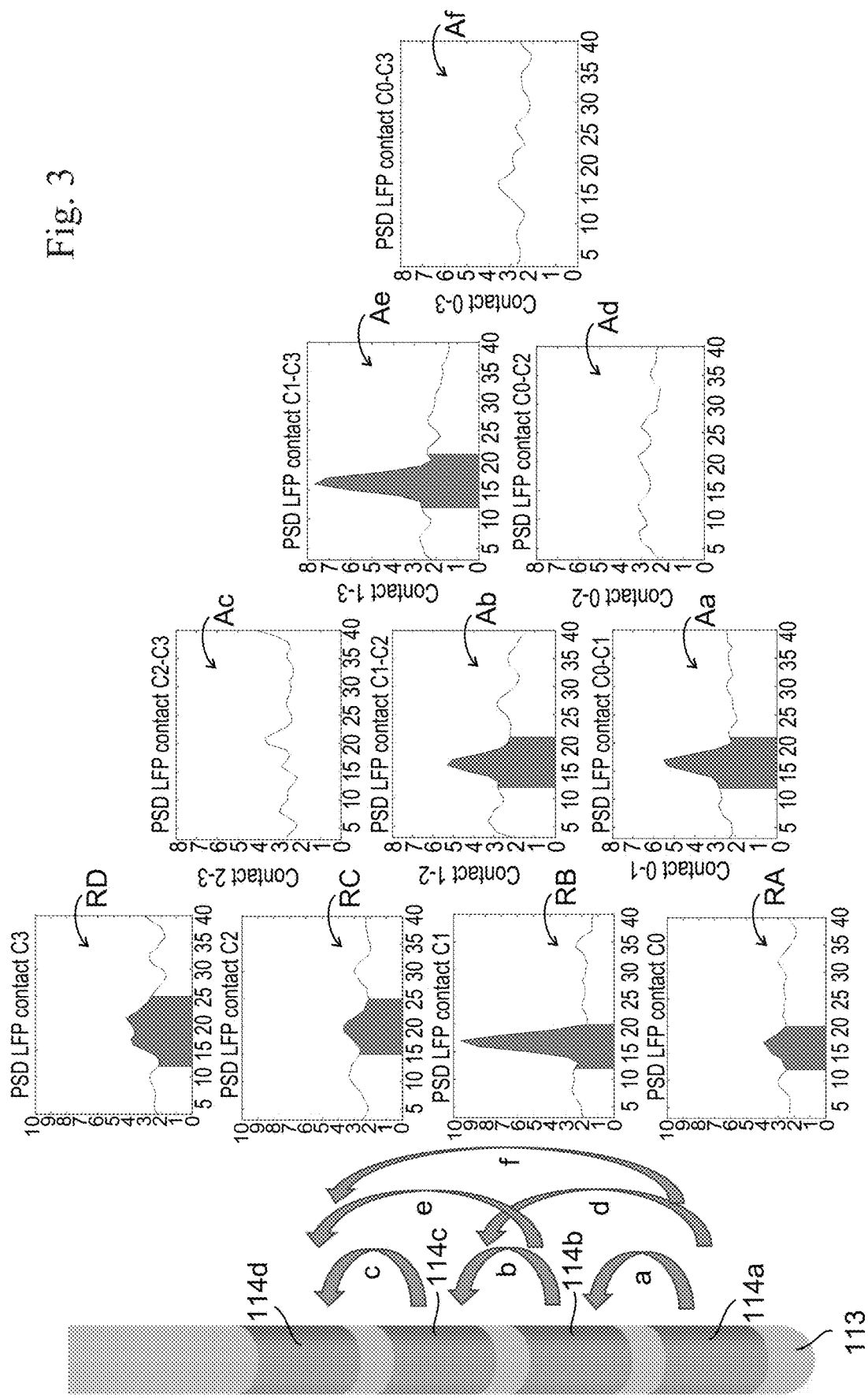
FIG. 3 is a schematic illustration of Bi-polar recordings between DBS Lead contacts, according to some embodiments of the invention.

Reference is now made to FIGS. 2A, 2B and 3 depicting recording from macro electrode contacts and microelectrodes, according to some exemplary embodiments of the invention.

According to some exemplary embodiments, for example as shown in FIG. 2A, readings are taken from one or more of the Macro contacts 114 of the DBS Lead 113, comprising, for example, 4 Macro contacts 114 in total. In some embodiments, the DBS lead 113 Macro contact 114 is e.g. about 1.5 mm in length, so in order to cover all the Microelectrode 101 data from same area (Microelectrode 101 moves in e.g. about 0.1 mm step size) an average for all Microelectrode 101 readings 115 from 15 sites is calculated and compared to a reading from 1 site recorded from Macro contact 114, for example reading Ra in FIG. 3.

Reference is now made to FIG. 2B, which shows an exemplary Average MER spiking activity at the DBS contact location. According to some exemplary embodiments, an analysis is performed on the DBS Lead 113 data, for example by calculating and plotting the Power spectrum density (PSD) of the SPK data for each signal, optionally after passing the data a full wave rectification to extract the low frequency from the data.

In some embodiments, the same analysis is performed on the Microelectrode 101 data but as multiple Microelectrode sites are needed to cover the DBS Lead 113 Macro contact 114 length, averaging of the PSD of all the readings from sites of Microelectrode 101 at depths overlapping with the position of the Macro contact 114 is performed, for example in order to obtain an equivalent result to the DBS Lead 113 Macro contact 114.

According to some exemplary embodiments, the same analysis is performed on both monopolar data (recording from a single electrode, with the voltage referenced to a relatively distant ground electrode) from the DBS Lead 113, and for Bipolar recordings (differential between two contacts in relative proximity, for example Microelectrode 101 and Macro contact 114, Microelectrode 101 and another Microelectrode 101, a $1^{st}$ Macro contact 114 and a 2nd Macro contact 114, Macro contact 114 and Micro contact 157 or any other combination of 2 different electrodes).

Reference is now made to FIG. 3, depicting Bipolar recordings of Macro contacts, for example macro contacts 114, according to some exemplary embodiments of the invention.

In some embodiments, reading Ra is a reading taken from Macro contact 114a, reading Rb is a reading taken from Macro contact 114b, reading Rc is a reading taken from Macro contact 114c, and reading Rd is a reading taken from Macro contact 114d.

According to some exemplary embodiments, average Aa is an average of readings Ra and Rb, average Ab is an average of readings Rb and Rc, average Ac is an average of readings Rc and Rd, average Ad is an average of averages Aa and Ab, average Ae is an average of averages Ab and Ac, and average Af is an average of averages Ad and Ae.

In some embodiments, the pairs of Rc and Ae, Rb and Ad and Ab and Af represent same depth. In some embodiments, each pair is averaged, resulting in 7 different depth points, as described for example in FIGS. 4A and 4B.

Figure 4A:
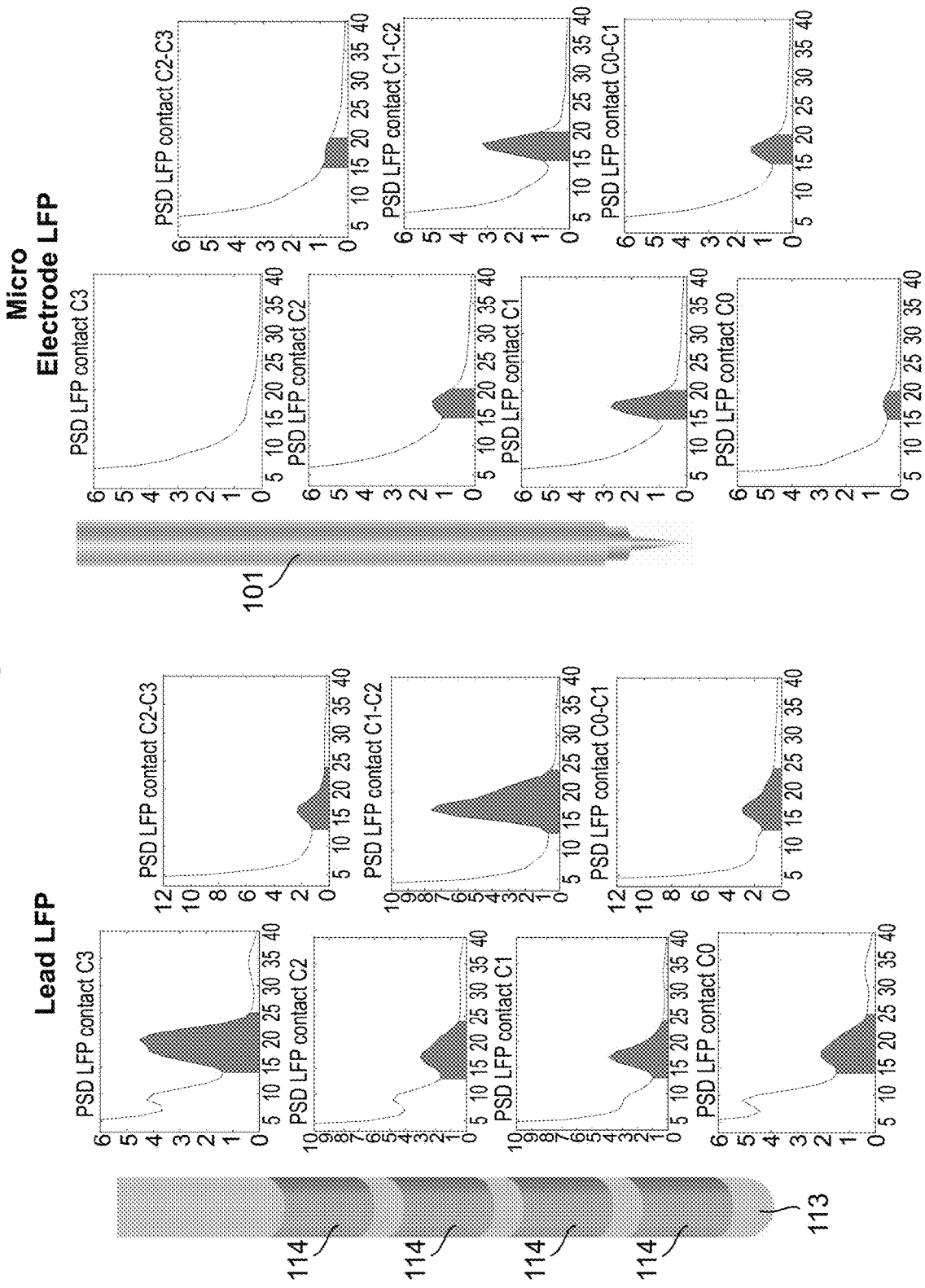
FIG. 4A is a schematic illustration of processed LFP readings from 4 DBS Lead contacts and processed LFP readings from microelectrodes, measured at 7 different depth locations, according to some embodiments of the invention.

According to some exemplary embodiments, for example as shown in FIG. 4A, data obtained from readings taken from Microelectrode 101 and Macro contacts 114 provides 7 different depth points in LFP frequency range.

According to some exemplary embodiments, for example as shown in FIG. 4B, data obtained from readings taken from Microelectrode 101 and Macro contacts 114 provides 7 different depth points in SPK frequency range.

Exemplary Similarity Measure Between LFP and SPK Readings

Figure 5:
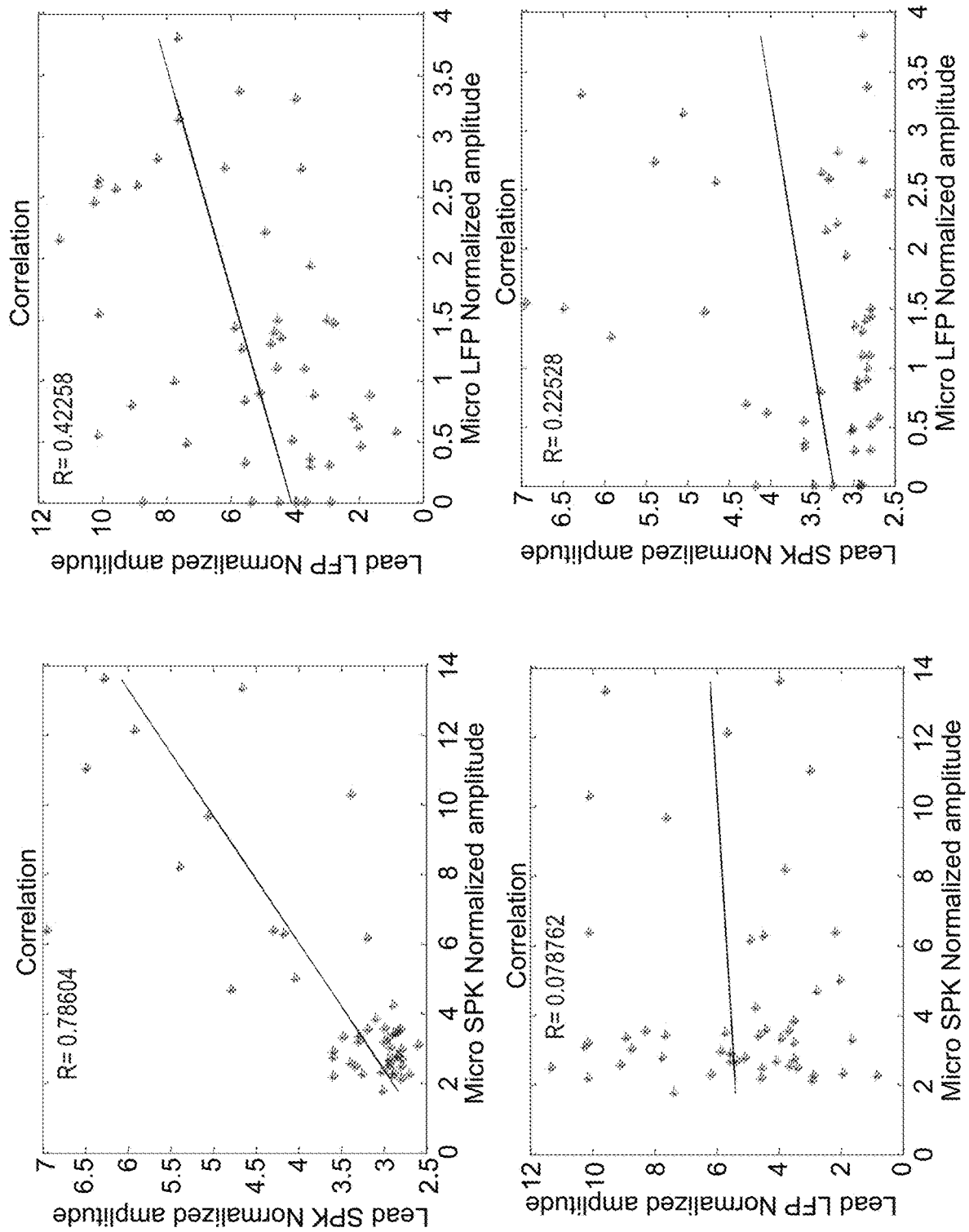
FIG. 5 is a graphic representation of results of correlation calculations between different sets of data including the LFP and SPK readings described in FIGS. 4A and 4B, according to some embodiments of the invention.

Reference is now made to FIG. 5 depicting a similarity measure between LFP and SPK data, according to some exemplary embodiments of the invention. In FIG. 5, the calculated similarity measure is the correlation measure.

According to some exemplary embodiments, for example as shown in FIG. 5, a similarity measure is calculated for each pair, including MicroSPK/LeadSPK, MicroLFP/LeadLFP, MicroSPK/LeadLFP and MicroLFP/LeadSPK. In some embodiments, the calculations include the following steps:

1—Microelectrode recording with high sampling rate (44 Khz) and filters (300-6000 Hz)

2—Record data from the lead with high sampling rate (44 Khz) and wide filtering (HW 0.07-9000 Hz)

3—Filter the SPK Lead data component from Lead data [300-6000 Hz] while keeping the sampling rate 44 Khz 4—Use the absolute value operator (Abs(x)=|x|) to perform full wave rectification of the data (sourced from both Microelectrode and Lead).

5—Calculate the power spectrum density out of the absolute data and normalize it by dividing the PSD value at each frequency bin by a normalization value, which may be the sum of PSD over the entire calculated frequency range.

6—Calculate the value of the maximum points in the PSD.

7—Correlate between the maximal values of the 7 PSD estimates obtained from each lead and MER as explained above.

8—Further compare the full graph and not only the maximum value. This may be done by applying a correlation calculation to the pair of compared PSDs, but also via other similarity measures, such as positive definite kernels (RBF as an example), cosine similarity or inverse of distance metrics as defined above.

According to some exemplary embodiments, for example as shown in FIG. 5 and in table 1 below, a high correlation between each pair indicates similar position, thus providing for better navigation, as the Neurosurgeon is able to determine the DBS Lead position similarity to Microelectrode position once a high degree of correlation between readings is obtained. For example, the following correlations could be achieved:

TABLE 1

Correlation values of DBS Lead and MicroElectrode LFP/Spike Recordings

| Combination | Correlation |
|---|---|
| Lead SPK-Micro SPK | 0.83 |
| Lead LFP-Micro LFP | 0.6 |
| Lead SPK-Micro LFP | 0.53 |
| Lead LFP-Micro SPK | 0.48 |

TABLE 2

Population (n = 7 trajectories) correlation values of DBS Lead and MicroElectrode LFP/Spike Recordings

| Combination | Correlation |
|---|---|
| Lead SPK-Micro SPK | 0.75 |
| Lead LFP-Micro LFP | 0.38 |
| Lead SPK-Micro LFP | 0.36 |
| Lead LFP-Micro SPK | 0.06 |

A potential advantage of having a high correlation between DBS Lead 113 SPK and Microelectrode 101 SPK readings may be the ability to (1) give confirmation for DBS Lead 113 positioning in the brain based on electrophysiology instead of imaging; and (2) recommend on repositioning of the DBS Lead 113 in the operation room in case of misplacement based on the comparison to the Microelectrode 101 Recording data. The recommendation can include Go/No Go output or degree of advancement output in steps or length units needed to reach the predetermined target.

In some embodiments, a similar procedure employs a calculation of the cross-correlation between the readings from the lead and staggered (shifted) averages of readings from the Microelectrode. For two vectors of discrete samples, f[n] and g[n], this is calculated by:

$$(f[n] * g[n]) = \frac{1}{r[n]} \sum_{m=-M}^{M} f[m]g[m+n]$$

Wherein M should be large enough to span the rang of interest where correlation is expected to be of interest, and r[n] is an normalization coefficient which may be identically equal to 1, or according to several well-known alternatives.

This is similar in principle to calculating multiple correlations between the lead readings (as an example let's assume N=7 readings) and multiple sets of averages of the Microelectrode recording, each set having N averages. Out of the multiple correlation calculations, the maximum cross-correlation value would indicate the shift between the lead position and the position that maximally correlates with the Microelectrode recording. This outcome may be used to recommend to the neurosurgeon to change the position of lead according to the shift size and shift direction corresponding to the maximal cross correlation between the lead readings and shifted Microelectrode average sets.

According to some exemplary embodiments, the SPK data from the DBS Lead 113 allows for example, to navigate and perform an alternative to a Microelectrode 101 Recording using the DBS Lead 113 and optionally getting similar results to Microelectrode 101. In some embodiments, measuring signals, for example SPK signals or a combination of SPK and LFP signals by one or more macro contacts of a DBS lead, allows for example, to use only the DBS Lead 113 to navigate in DBS surgeries instead of using the Microelectrode 101. According to this embodiment and other embodiments, the lead is inserted in the brain to some depth above the imaging-based anatomic depth, and then a process of navigation is initiated.

According to some exemplary embodiments, in this process, readings from the lead contacts are obtained at a sequence of steps, and PSDs of these readings are calculated. In some embodiments, the resulting PSDs are either displayed for the user to analyze or are compared with some prior prototype of the target region PSD profile, or both. In some embodiments, the sequence of readings steps may be real, corresponding to a sequence of steps in which the lead is moved. Alternatively, the sequence of readings steps is virtual, and while the lead is moved continually, without stopping at specific sites, data from nearby depths are bundled and analyzed as if they were recorded at a single position that is the center of the nearby depths range. In some embodiments, once the navigation process is completed, the site from which the lead reading PSD best corresponds to a PSD profile corresponding to optimal stimulation outcomes is selected as the implantation depth. In some embodiments, once selected, test stimulation may optionally be performed at the selected site for example, for verification of symptom severity reduction and/or identification of troublesome stimulation side effects. Finally, the lead may be fixed at the selected site to provide therapeutic stimulation.

According to some exemplary embodiments, during the process described above one or more decisions are being made. In some embodiments, one decision is a repeated selection of step size or advancement rate, which embodies a tradeoff between mapping accuracy and time consumed for completing the process. Alternatively, or additionally, another decision is at which stage to terminate the navigation phase. Terminating too soon may lead to missing a deeper site with a better outcome potential, while inserting the lead into neural structures outside the range that it is necessary to map would lead to unnecessary damage to the brain tissue. In some embodiments, the decision includes deciding which site would lead to optimal outcome. For each of these decisions there are several alternatives. The $1^{st}$ alternative, in some embodiments, is that the user would make the decision, based on their knowledge and experience. A $2^{nd}$ alternative, in some embodiments, is that the decision would be made according to a prescribed set of rules embedded in the system software or hardware, such as: "if the average PSD at 12-30 Hz is 3 times larger than the average PSD obtained at the highest depth (or several depths), then decrease step size (or continuous advancement rate) to e.g. 0.1 mm", or "if the average PSD at 12-30 Hz is 3 times smaller than the maximal average PSD obtained along the trajectory the stop the navigation phase", or "select the depth which maximizes the average SD at 12-30 Hz for any pair of macro contacts". Such a set can be derived based on the experience of expert users, and/or based on research of the outcomes of lead implantations and the recording during the surgery.

A 3rd alternative, in some embodiments, would be to employ one of the many methods known as "machine learning" methods, in which a set of inputs (readings) is provided to an algorithm together with a corresponding set of labels (outcomes), and the algorithm learns to compute a prediction from future inputs, predicting their corresponding outcome. This approach can apply for any of the 3 decision types that are required during the navigation phase. Suitable machine learning algorithms include support vector machines, dynamic Bayesian networks, hidden Markov models, decision trees, and neural networks, including deep neural networks and convolutional neural networks. It is expected that during the life of a patent maturing from this application many relevant leads will be developed; the scope of the term leads is intended to include all such new technologies a priori.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. A method for determining position of an electrode lead inside a body tissue, comprising:
   receiving electrical signals recorded from at least one macro electrode contact of an electrode lead positioned inside a body tissue;
   extracting spiking (SPK) signals from said received electrical signals, wherein said extracting comprises filtering said received electrical signals to obtain said SPK signals within a frequency range of 250 Hz-7000 Hz;
   providing stored measurements or indications thereof;
   determining a position of said lead and/or said at least one macro electrode contact inside said body tissue based on said extracted SPK signals and said provided stored measurements or indications thereof.

2. A method according to claim 1, wherein said extracting comprises reconstructing a waveform from said obtained said SPK signals.

3. A method according to claim 2, wherein said reconstructing comprises applying a full wave rectification algorithm on said SPK signals.

4. A method according to claim 1, comprising:
   measuring at least one parameter of said extracted spiking signals, and wherein said determining a position comprises determining a relative position of said electrode lead and/or said at least one macro electrode contact inside said body tissue based on said measured at least one parameter and said provided stored measurements or indications thereof.

5. A method according to claim 4, wherein said at least one parameter of said extracted spiking signals comprises at least one of power spectrum density (PSD), normalized PSD, Amplitude, Power, Frequency, Spike detection, Audio, Area under a curve, root mean square (RMS) and firing rate.

6. A method according to claim 4, comprising:
   delivering a human detectable indication according to a relation between said determined relative position and a desired anatomical target.

7. A method according to claim 6, wherein said delivering comprises delivering instructions regarding at least one of advancement speed of said electrode lead, advancement step size of said electrode lead, advancement direction of said electrode lead, according to said relation.

8. A method according to claim 1, wherein said provided stored measurements or indications thereof are measured by at least one microelectrode inside said body tissue.

9. A method according to claim 1, wherein said determined position is a position relative to at least one of, a position inside said body tissue, a position along an insertion trajectory of said electrode lead inside the body tissue, a position of an entry point of said lead into a skull, and a position of an entry point of said lead into a brain.

10. A method according to claim 1, wherein said stored measurements or indications thereof comprise SPK measurements or indications thereof, or LFP measurements or indications thereof.

11. A method according to claim 1, comprising:
    determining a correlation between said extracted spiking signals and said stored measurements or indications thereof, and wherein said determining said position comprises determining said position based on said determined correlation.

12. A method according to claim 1, wherein said body tissue comprises the brain, and wherein said lead comprises a DBS lead configured to deliver an electric stimulation to brain tissue.

13. A system for determining a position of a lead inside a subject body, comprising:
    an implantable lead insertable via an insertion trajectory through body tissue, comprising at least one macro electrode contact configured to record electrical signals from tissue surrounding said implantable lead;
    a control unit connectable to said implantable lead, comprising:
    a memory, wherein said memory stores one or more indications including a relation between a position in said body tissue and electrical measurements or indications thereof;
    a control circuitry connected to said at least one macro electrode, wherein said control circuitry is configures to:
    receive electrical signals recorded by said at least one macro-electrode contact;
    extract SPK signals from said received electrical signals by filtering said received electrical signal with a filter which extracts electrical signals within a frequency range of 250 Hz-7000 Hz;
    measure values of at least one SPK parameter from said extracted SPK signals;
    determine a position of said implantable lead and/or said macro electrode contact in said body using said measured at least one SPK parameter and said stored indications.

14. A system according to claim 13, wherein said control circuitry is configured to calculate a relation value between said measured SPK signals and one or more indications stored in said memory, and to determine a position of said implantable lead in said body based on said calculated relation value.

15. A system according to claim 13, wherein said at least one SPK parameter comprises at least one of power spectrum density (PSD), amplitude, power, frequency, spike detection, Audio, Area under a curve, root mean square (RMS) and firing rate.

16. A system according to claim 13, wherein said control circuitry is configured to:
   extract LFP signals from said received electrical signals;
   measure values of at least one LFP parameter from said extracted LFP signals;
   determine a position of said implantable lead and/or said macro electrode contact in said body using said measured at least one LFP parameter and said stored indications.

17. A system according to claim 16, wherein said control circuitry is configured to:
   calculate a first correlation value between said at least one measured SPK parameter and said stored indications, and a second correlation value between said at least one measured LFP parameter and said stored indications;
   select a correlation with the highest correlation value from said first correlation value and said second correlation value; and
   determine a position of said lead and/or said at least one macro electrode contact based on said selected correlation.

18. A system according to claim 13, comprising:
   a user interface configured to deliver at least one human detectable indication to a user of the system; and
   wherein said control circuitry signals said user interface to generate said human detectable indication according to said determined position.

19. A system according to claim 18, wherein said at least one human detectable indication comprises recommendations regarding an advancement speed of the lead, an advancement direction of said lead, an advancement step size.

20. A system according to claim 13, comprising:
   at least one microelectrode insertable into said body tissue;
   wherein said control circuitry is connected to said at least one microelectrode, and is configured to:
   receive electrical signals recorded by said at least one microelectrode in said body tissue;
   extract SPK signals and/or LFP signals from said received electrical signals;
   measure at least one SPK parameter and/or at least one LFP parameter from said extracted SPK signals and/or said extracted LFP signals;
   store in said memory said measured at least one SPK parameter and/or said at least one LFP parameter as said one or more indications.

* * * * *

UNITED STATES PATENT AND TRADEMARK OFFICE
CERTIFICATE OF CORRECTION

PATENT NO. : 12,070,278 B2  
APPLICATION NO. : 17/622337  
DATED : August 27, 2024  
INVENTOR(S) : Hagai Bergman et al.

Page 1 of 1

It is certified that error appears in the above-identified patent and that said Letters Patent is hereby corrected as shown below:

On the Title Page

Insert the following:
-- (62) Related U.S. Application Data
Provisional application No. 62/867,222 filed on Jun. 26, 2019. --

Signed and Sealed this
Fifteenth Day of July, 2025

Coke Morgan Stewart
*Acting Director of the United States Patent and Trademark Office*